US012697031B2

(12) United States Patent
Agrawal et al.

(10) Patent No.: US 12,697,031 B2
(45) Date of Patent: Aug. 4, 2026

(54) PHOTOACOUSTIC DEVICES AND SYSTEMS INCLUDING SURFACE WAVE SENSING COMPONENTS

(71) Applicant: QUALCOMM Incorporated, San Diego, CA (US)

(72) Inventors: Sumit Agrawal, Sunnyvale, CA (US); Hrishikesh Vijaykumar Panchawagh, Cupertino, CA (US); Ali Lopez, Dublin, CA (US); Kostadin Dimitrov Djordjev, Los Gatos, CA (US); Camilo Perez Saaibi, Dublin, CA (US); Nicholas Buchan, San Jose, CA (US)

(73) Assignee: QUALCOMM Incorporated, San Diego, CA (US)

( * ) Notice: Subject to any disclaimer, the term of this patent is extended or adjusted under 35 U.S.C. 154(b) by 198 days.

(21) Appl. No.: 18/319,414

(22) Filed: May 17, 2023

(65) Prior Publication Data

US 2024/0197186 A1     Jun. 20, 2024

Related U.S. Application Data

(60) Provisional application No. 63/476,346, filed on Dec. 20, 2022.

(51) Int. Cl.
    *A61B 5/00*     (2006.01)
    *A61B 5/02*     (2006.01)
(52) U.S. Cl.
    CPC .......... *A61B 5/0095* (2013.01); *A61B 5/0044* (2013.01); *A61B 5/02007* (2013.01); *A61B 5/6826* (2013.01)
(58) Field of Classification Search
    CPC . A61B 5/0095; A61B 5/0044; A61B 5/02007; A61B 5/6826; A61B 5/489
    See application file for complete search history.

(56) References Cited

U.S. PATENT DOCUMENTS 4,100,811 A * 7/1978 Cullen .................. G01L 9/0025
                                              73/609
7,088,455 B1 * 8/2006 Kirkpatrick ........ G01N 21/1717
                                              356/502
(Continued)

FOREIGN PATENT DOCUMENTS

CN         107367462 B  * 12/2019   ......... G01N 21/1702
CN         111436910 B  * 7/2023   .......... A61B 5/0066
(Continued)

OTHER PUBLICATIONS

International Search Report and Written Opinion—PCT/US2023/078812—ISA/EPO—Mar. 11, 2024.

*Primary Examiner* — Kaitlyn E Sebastian
(74) *Attorney, Agent, or Firm* — QUALCOMM Incorporated

(57)          ABSTRACT

An apparatus may include a substrate, a light source system and a receiver system. The light source system may be configured to emit light through an area of the substrate, from a first side of the substrate towards a target object in contact with a second and opposite side of the substrate. The receiver system may include one or more receivers residing in, on or proximate the substrate. The receiver system may be configured to detect surface acoustic waves propagating in the substrate corresponding to a photoacoustic response of the target object to light emitted by the light source system. In some examples, the apparatus may include a control system. The control system may be configured to receive surface acoustic wave signals from the receiver system corresponding to detected surface acoustic waves and to detect at least one structure within the target object based on the surface acoustic wave signals.

42 Claims, 13 Drawing Sheets

(56)                    References Cited

U.S. PATENT DOCUMENTS

| | | | | |
|---|---|---|---|---|
| 9,211,068 | B2 | 12/2015 | Furukawa | |
| 9,435,730 | B2 | 9/2016 | Nishihara | |
| 11,234,648 | B2 | 2/2022 | Ogawa et al. | |
| 2002/0108445 | A1* | 8/2002 | Wooh | G01N 29/4427 |
| | | | | 73/634 |
| 2003/0010898 | A1 | 1/2003 | Mackenzie et al. | |
| 2011/0208066 | A1 | 8/2011 | Gnadinger | |
| 2012/0116227 | A1* | 5/2012 | Suzuki | G01S 7/52073 |
| | | | | 600/443 |
| 2013/0121106 | A1 | 5/2013 | Nishihara | |
| 2013/0333094 | A1* | 12/2013 | Rogers | A61B 34/76 |
| | | | | 340/407.1 |
| 2017/0323131 | A1* | 11/2017 | Lu | G06V 40/10 |
| 2017/0323132 | A1* | 11/2017 | Lu | A61B 5/0095 |
| 2018/0165566 | A1* | 6/2018 | Rogers | H02J 50/001 |
| 2020/0143534 | A1* | 5/2020 | Wright | G06T 7/0012 |
| 2022/0175258 | A1 | 6/2022 | Kitchens et al. | |

FOREIGN PATENT DOCUMENTS

| | | | |
|---|---|---|---|
| WO | 2015054688 | A9 | 8/2015 |
| WO | WO2015118880 | A1 | 8/2015 |

* cited by examiner

600

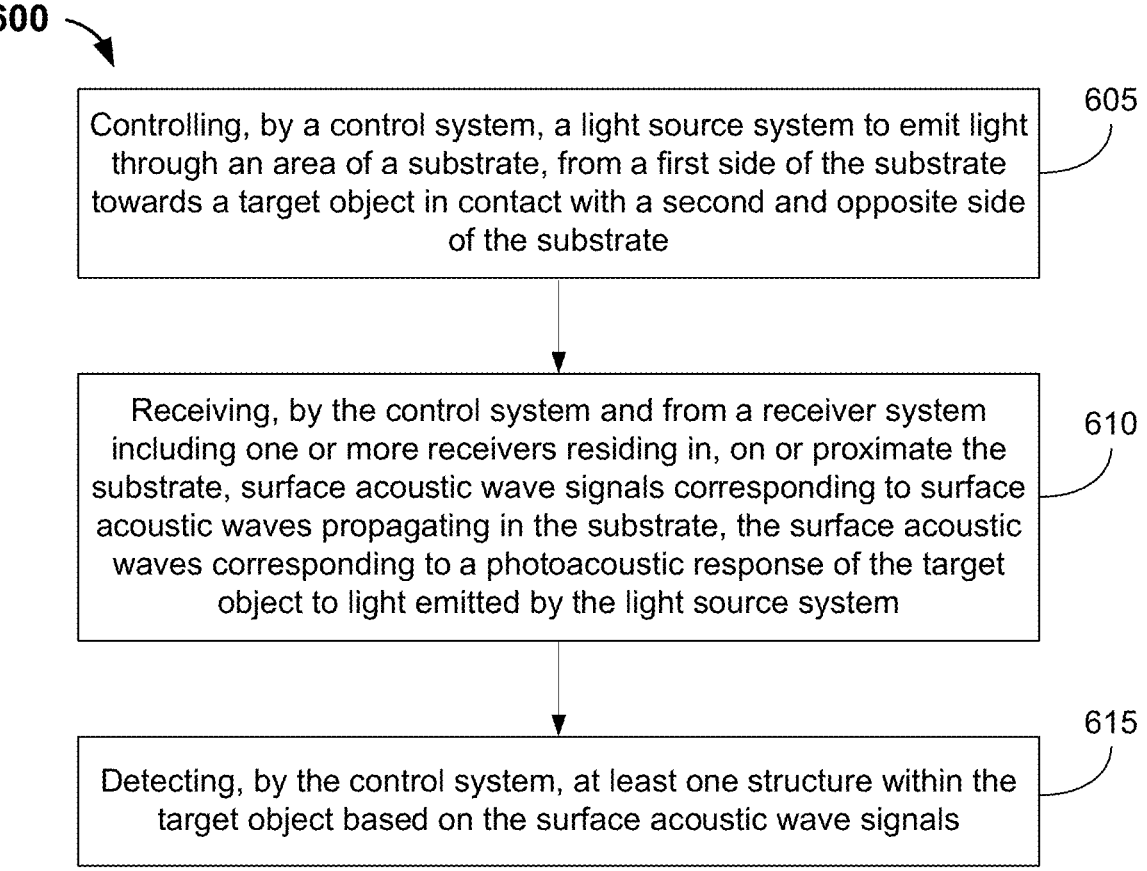

Controlling, by a control system, a light source system to emit light through an area of a substrate, from a first side of the substrate towards a target object in contact with a second and opposite side of the substrate

605

Receiving, by the control system and from a receiver system including one or more receivers residing in, on or proximate the substrate, surface acoustic wave signals corresponding to surface acoustic waves propagating in the substrate, the surface acoustic waves corresponding to a photoacoustic response of the target object to light emitted by the light source system

610

Detecting, by the control system, at least one structure within the target object based on the surface acoustic wave signals

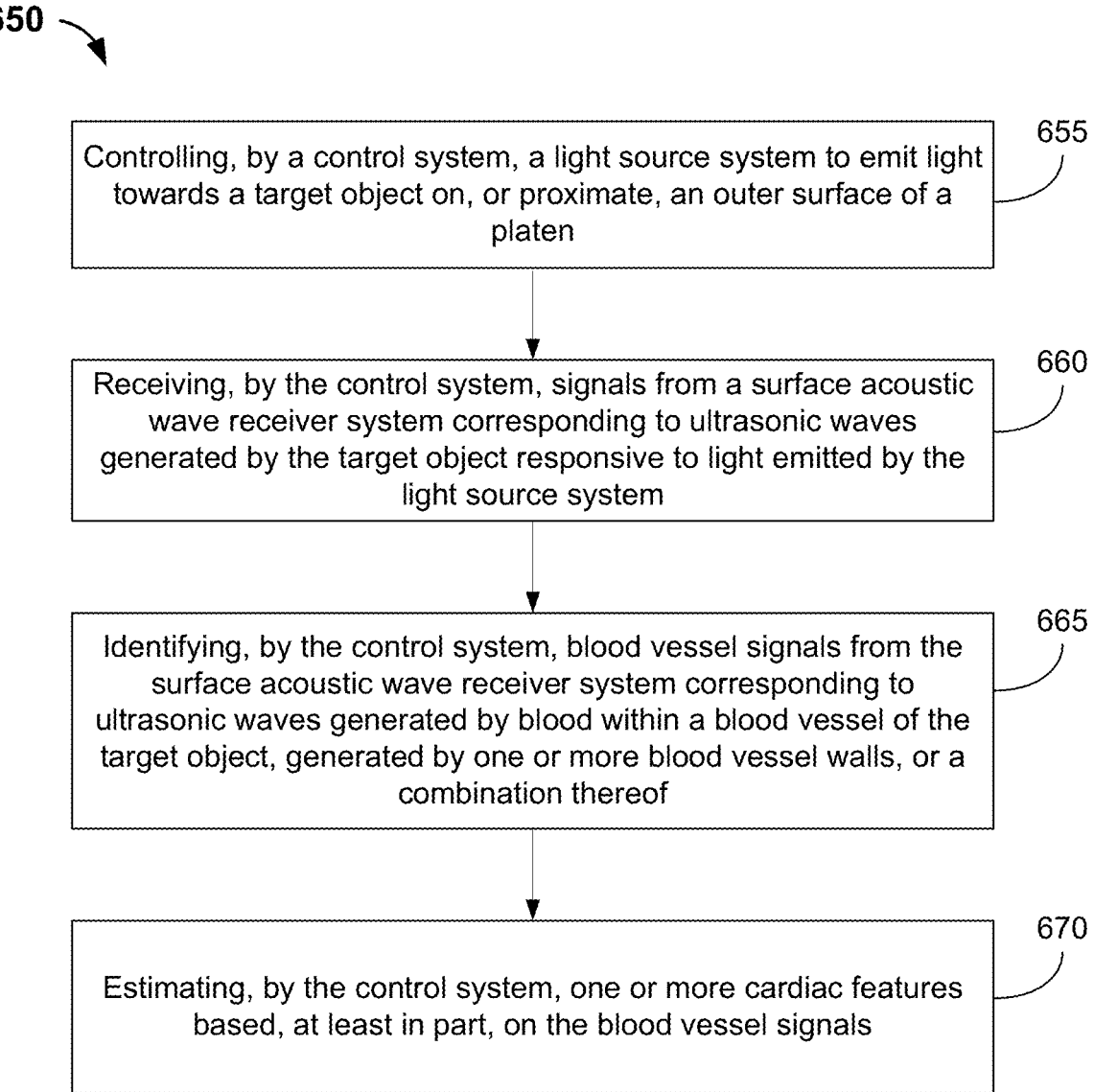

655
Controlling, by a control system, a light source system to emit light towards a target object on, or proximate, an outer surface of a platen 660
Receiving, by the control system, signals from a surface acoustic wave receiver system corresponding to ultrasonic waves generated by the target object responsive to light emitted by the light source system 665
Identifying, by the control system, blood vessel signals from the surface acoustic wave receiver system corresponding to ultrasonic waves generated by blood within a blood vessel of the target object, generated by one or more blood vessel walls, or a combination thereof 670
Estimating, by the control system, one or more cardiac features based, at least in part, on the blood vessel signals

*Figure 6B*

PHOTOACOUSTIC DEVICES AND SYSTEMS INCLUDING SURFACE WAVE SENSING COMPONENTS

PRIORITY CLAIM

This application claims priority to U.S. Provisional Patent Application No. 63/476,346, filed on Dec. 20, 2022 and entitled "PHOTOACOUSTIC DEVICES AND SYSTEMS INCLUDING SURFACE WAVE SENSING COMPO-NENTS," which is hereby incorporated by reference and for all purposes.

TECHNICAL FIELD

This disclosure relates generally to photoacoustic devices and systems.

DESCRIPTION OF RELATED TECHNOLOGY

A variety of different sensing technologies and algorithms are being implemented in devices for various biometric and biomedical applications, including health and wellness monitoring. This push is partly a result of the limitations in the usability of traditional measuring devices for continuous, noninvasive and ambulatory monitoring. Some such devices are, or include, photoacoustic devices. Although some pre-viously-deployed photoacoustic devices and systems can provide acceptable results, improved photoacoustic devices and systems would be desirable.

SUMMARY

The systems, methods and devices of this disclosure each have several aspects, no single one of which is solely responsible for the desirable attributes disclosed herein.

One innovative aspect of the subject matter described in this disclosure can be implemented in an apparatus. In some implementations, a mobile device (such as a wearable device, a cellular telephone, etc.) may be, or may include, at least part of the apparatus.

According to some examples, the apparatus may include a substrate, a light source system and a receiver system. In some examples, the light source system may be configured to emit light through an area of the substrate, from a first side of the substrate towards a target object in contact with a second and opposite side of the substrate. In some examples, the receiver system may include one or more receivers residing in, on or proximate the substrate. According to some examples, the receiver system may be configured to detect surface acoustic waves propagating in the substrate corresponding to a photoacoustic response of the target object to light emitted by the light source system.

In some implementations, the apparatus may include a control system. The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combi-nations thereof. According to some examples, the control system may be configured to receive surface acoustic wave signals from the receiver system corresponding to detected surface acoustic waves and to detect at least one structure within the target object based on the surface acoustic wave signals.

According to some examples, the at least one structure may be a blood vessel structure. In some examples, the control system may be further configured to estimate one or more cardiac-related features based, at least in part, on the at least one structure.

In some examples, the light source system may be con-figured to emit laser pulses. In some such examples, the light source system may be configured to emit the laser pulses at pulse widths in a range from 3 nanoseconds to 1000 nano-seconds. In some examples, the laser pulses may be in a wavelength range of 500 nm to 1000 nm.

According to some examples, the substrate may be trans-parent. In some examples, the substrate may include piezo-electric material.

In some examples, the combined thickness of the sub-strate and the light source system may be in a range from 2 mm to 5 mm. According to some examples, the thickness of the substrate may be in a range from 0.5 mm to 1.0 mm. In some examples, the total area of the substrate may be in a range from 0.5 cm$^2$ to 2.0 cm$^2$.

According to some examples, the receiver system may include piezoelectric material. In some examples, the receiver system may include at least one receiver element on the first side of the substrate. According to some examples, the receiver system may include at least one receiver ele-ment offset laterally from the area of the substrate in a first direction and at least one receiver element offset laterally from the area of the substrate in a second and opposite direction. In some examples, the receiver system may include at least one interdigital transducer.

In some examples, the control system may be further configured to detect blood within a blood vessel based on the surface acoustic wave signals. According to some examples, the blood vessel may be an artery.

According to some examples, the photoacoustic response may produce target object acoustic waves within the target object. In some such examples, at least a portion of the target object acoustic waves may be converted to the surface acoustic waves propagating in the substrate. In some examples, the target object acoustic waves may include longitudinal ultrasonic acoustic waves.

In some examples, the apparatus may include a substrate, a light source system and a receiver system. In some examples, the light source system may be configured to emit light through an area of the substrate, from a first side of the substrate towards a target object in contact with a second and opposite side of the substrate. In some examples, the receiver system may include one or more receivers residing in, on or proximate the substrate. According to some examples, the receiver system may be configured to selec-tively detect one or more specific types of surface acoustic waves propagating in the substrate corresponding to a pho-toacoustic response of the target object to light emitted by the light source system.

According to some examples, the piezoelectric material may include a type of piezoelectric crystal that enhances a sensitivity of the receiver system to one or more particular types of surface acoustic waves. In some such examples, the crystal may have a piezo-crystal cut that enhances the sensitivity of the receiver system to the one or more par-ticular types of surface acoustic waves.

In some examples, the receiver system may include at least one interdigital transducer. According to some examples, the receiver system may include piezoelectric material.

Other innovative aspects of the subject matter described in this disclosure can be implemented in a method. In some examples, the method may involve controlling, by a control system, a light source system to emit light through an area of a substrate, from a first side of the substrate towards a target object in contact with a second and opposite side of the substrate. In some examples, the method may involve receiving, by the control system and from a receiver system including one or more receivers residing in, on or proximate the substrate, surface acoustic wave signals corresponding to surface acoustic waves propagating in the substrate. The surface acoustic waves may correspond to a photoacoustic response of the target object to light emitted by the light source system. In some examples, the method may involve detecting, by the control system, at least one structure within the target object based on the surface acoustic wave signals.

In some examples, the method may involve estimating one or more cardiac-related features based, at least in part, on the at least one structure. According to some examples, controlling the light source system may involve controlling the light source system to emit laser pulses. In some examples, the at least one structure may be a blood vessel structure.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in one or more non-transitory media having software stored thereon. The software may include instructions for controlling one or more devices to perform one or more disclosed methods.

In some examples, the method may involve controlling, by a control system, a light source system to emit light through an area of a substrate, from a first side of the substrate towards a target object in contact with a second and opposite side of the substrate. In some examples, the method may involve receiving, by the control system and from a receiver system including one or more receivers residing in, on or proximate the substrate, surface acoustic wave signals corresponding to surface acoustic waves propagating in the substrate. The surface acoustic waves may correspond to a photoacoustic response of the target object to light emitted by the light source system. In some examples, the method may involve detecting, by the control system, at least one structure within the target object based on the surface acoustic wave signals.

In some examples, the method may involve estimating one or more cardiac-related features based, at least in part, on the at least one structure. According to some examples, controlling the light source system may involve controlling the light source system to emit laser pulses. In some examples, the at least one structure may be a blood vessel structure.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

FIG. 6A is a flow diagram that shows examples of some disclosed operations.

FIG. 6B is a flow diagram that shows examples of some additional disclosed operations.

Like reference numbers and designations in the various drawings indicate like elements.

DETAILED DESCRIPTION

Figure 1:
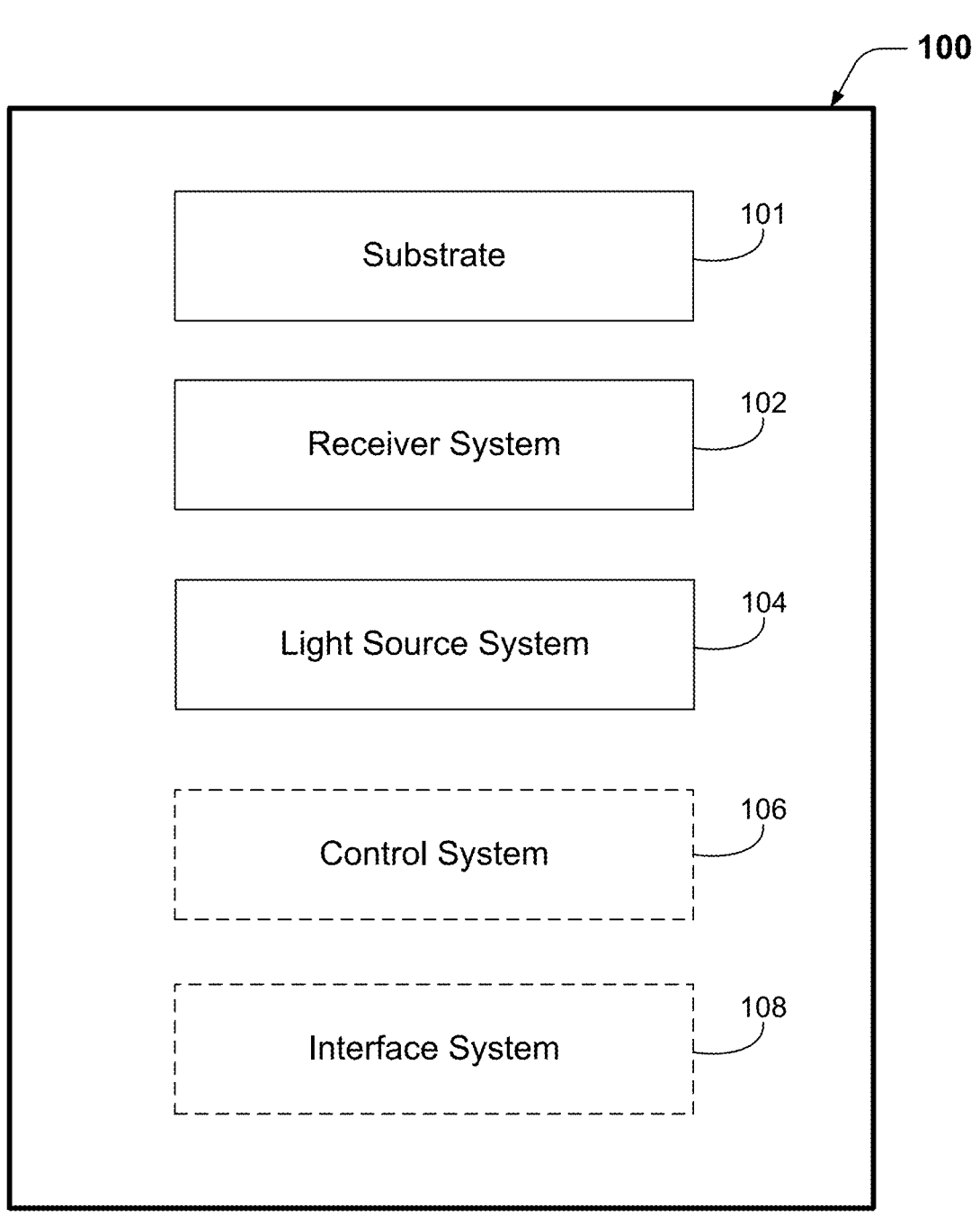
FIG. 1 is a block diagram that shows example components of an apparatus according to some disclosed implementations.

The following description is directed to certain implementations for the purposes of describing various aspects of this disclosure. However, a person having ordinary skill in the art will readily recognize that the teachings herein can be applied in a multitude of different ways. Some of the concepts and examples provided in this disclosure are especially applicable to blood pressure monitoring applications. However, some implementations also may be applicable to other types of biological sensing applications, as well as to other fluid flow systems. The described implementations may be implemented in any device, apparatus, or system that includes an apparatus as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, handheld or portable computers, netbooks, notebooks, smartbooks, tablets, printers, copiers, scanners, facsimile devices, global positioning system (GPS) receivers/navigators, cameras, digital media players, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), architectural structures, microwaves, refrigerators, stereo systems, cassette recorders or players, DVD players, CD players, VCRs, radios, portable memory chips, washers, dryers, washer/dryers, parking meters, automobile doors, autonomous or semi-autonomous vehicles, drones, Internet of Things (IoT) devices, etc. Thus, the teachings are not intended to be limited to the specific implementations depicted and described with reference to the drawings; rather, the teachings have wide applicability as will be readily apparent to persons having ordinary skill in the art.

Non-invasive health monitoring devices, including but not limited to devices configured for photoacoustic plethysmography (PAPG), have various potential advantages over more invasive health monitoring devices such as cuff-based or catheter-based blood pressure measurement devices. However, it has proven to be difficult to design satisfactory PAPG-capable health monitoring devices. For example, some PAPG-capable devices that have recently been developed by the present assignee are advantageously configured to mitigate artifact signals such as electromagnetic interference (EMI) signals, signals from reflected light and signals from reflected acoustic waves. However, some such devices may be too large to deploy conveniently in a wearable device, such as a watch, a patch or an ear bud.

Some disclosed devices include a substrate, a light source system and a receiver system. The receiver system may be, or may include, a surface acoustic wave receiver system. According to some implementations, the light source system may be configured to emit light towards a target object, such as a finger or a wrist. The emitted light may include laser pulses. The receiver system may be configured to detect surface acoustic waves propagating in the substrate corresponding to a photoacoustic response of the target object to the emitted light. According to some examples, the device may include a control system. The control system may be configured to receive surface acoustic wave signals from the receiver system corresponding to detected surface acoustic waves. The control system may be configured to detect at least one structure within the target object based on the surface acoustic wave signals. The at least one structure may be a blood vessel structure, such as an arterial structure. In some examples, the control system may be configured to detect changes in an artery, such as changes in a diameter of the artery, changes in arterial distension, etc., corresponding to phases of the cardiac cycle. The detected structure(s), or changes thereof, may be used for various applications, for example for the estimation of cardiac-related features such as blood pressure. Accordingly, some disclosed devices may be PAPG-capable.

Particular implementations of the subject matter described in this disclosure can be implemented to realize one or more of the following potential advantages. Various disclosed configurations include PAPG-capable devices that are compact enough to reside in a wearable device. At least in part because the disclosed devices are configured to detect surface acoustic waves, the corresponding arrangements of the light source system, the substrate and the receiver system allow for the implementation of very thin, compact and lightweight devices, for example between 2 mm and 5 mm in overall thickness.

FIG. 1 is a block diagram that shows example components of an apparatus according to some disclosed implementations. In this example, the apparatus 100 includes a substrate 101, a receiver system 102 and a light source system 104. Some implementations of the apparatus 100 may include a control system 106, an interface system 108, or both.

The substrate 101 may include various materials, such as glass, acrylic, polycarbonate, etc. At least a portion of the substrate, through which the light source system provides light, should include transparent material such as polycarbonate, glass, etc. According to some implementations, at least a portion of the substrate may include piezoelectric material, such as lithium niobate ($LiNO_3$), lead magnesium niobate-lead titanate (PMM-PT), quartz, etc.

At least a portion of the outer surface of the substrate 101 may, for example, be configured to receive a target object, such as a human digit. (As used herein, the terms "finger" and "digit" may be used interchangeably, such that a thumb is one example of a finger.)

In some examples, the substrate 101 may have a thickness in the range from 0.1 mm to 2 mm. According to some examples, at least the outer surface of the substrate 101 may have an acoustic impedance that is configured to contrast with an acoustic impedance of human skin. For example, the acoustic impedance of the substrate 101 may be configured to be substantially greater than that of human skin. A typical range of acoustic impedances for human skin is 1.53-1.680 MRayls ($1,530\text{-}1,680\times10^3$ kg/(seconds m$^2$)). In some examples, the substrate 101 may include a substance having an acoustic impedance that is in the range of 2.5-16.0 MRayls ($2,500\text{-}16,000\times10^3$ kg/(seconds m$^2$)), such as polycarbonate, glass, quartz or another piezoelectric crystal, etc.

In some examples, the light source system 104 may be configured to emit light through an area of the substrate 101, from a first side of the substrate 101 towards a target object in contact with a second and opposite side of the substrate 101. According to some examples, the light source system 104 may be configured to emit laser pulses. The light source system 104 may, in some examples, include one or more light-emitting diodes. In some implementations, the light source system 104 may include one or more laser diodes. According to some implementations, the light source system 104 may include one or more vertical-cavity surface-emitting lasers (VCSELs). In some implementations, the light source system 104 may include one or more edge-emitting lasers. In some implementations, the light source system may include one or more neodymium-doped yttrium aluminum garnet (Nd:YAG) lasers. In some such examples, the light source system 104 may be configured to emit laser pulses at pulse widths in a range from 3 nanoseconds to 1000 nanoseconds.

In some examples, the light source system 104 may be configured to emit laser pulses in a wavelength range of 500 nm to 1000 nm. The light source system 104 may, in some examples, be configured to transmit light in one or more wavelength ranges. In some examples, the light source system 104 may configured for transmitting light in a wavelength range of 500 to 600 nanometers (nm). According to some examples, the light source system 104 may configured for transmitting light in a wavelength range of 800 to 950 nm. In view of factors such as skin reflectance, fluence, the absorption coefficients of blood and various tissues, and skin safety limits, one or both of these wavelength ranges may be suitable for various use cases. For example, the wavelength ranges of 500 nm to 600 nm and of 800 to 950 nm may both be suitable for obtaining photoacoustic responses from relatively smaller, shallower blood vessels, such as blood vessels having diameters of approximately 0.5 mm and depths in the range of 0.5 mm to 1.5 mm, such as may be found in a finger. The wavelength range of 800 to 950 nm may, for example, be suitable for obtaining photoacoustic responses from relatively larger, deeper blood vessels, such as blood vessels having diameters of approximately 2.0 mm and depths in the range of 2 mm to 3 mm, such as may be found in an adult wrist. In some implementations, the light source system 104 may be configured for emitting various wavelengths of light, which may be selectable to trigger acoustic wave emissions primarily from a particular type of material. For example, because the hemoglobin in blood absorbs near-infrared light very strongly, in some implementations the light source system 104 may be configured for emitting one or more wavelengths of light in the near-infrared range, in order to trigger acoustic wave emissions from hemoglobin. However, in some examples the control system 106 may control the wavelength(s) of light emitted by the light source system 104 to preferentially induce acoustic waves in blood vessels, other soft tissue, and/or bones. For example, an infrared (IR) light-emitting diode LED may be selected and a short pulse of IR light emitted to illuminate a portion of a target object and generate acoustic wave emissions that are then detected by the receiver system 102. In another example, an IR LED and a red LED or other color such as green, blue, white or ultraviolet (UV) may be selected and a short pulse of light emitted from each light source in turn with ultrasonic images obtained after light has been emitted from each light source. In other implementations, one or more light sources of different wavelengths may be fired in turn or simultaneously to generate acoustic emissions that may be detected by the surface acoustic wave receiver. Image data from the surface acoustic wave receiver that is obtained with light sources of different wavelengths and at different depths (e.g., obtained by varying range gate delays (RGDs)) into the target object may be combined to determine the location and type of material in the target object. Image contrast may occur as materials in the body generally absorb light at different wavelengths differently. As materials in the body absorb light at a specific wavelength, they may heat differentially and generate acoustic wave emissions with sufficiently short pulses of light having sufficient intensities. Depth contrast may be obtained with light of different wavelengths and/or intensities at each selected wavelength. That is, successive images may be obtained at a fixed RGD (which may correspond with a fixed depth into the target object) with varying light intensities and wavelengths to detect materials and their locations within a target object. For example, hemoglobin, blood glucose or blood oxygen within a blood vessel inside a target object such as a finger may be detected photoacoustically.

According to some examples, the receiver system 102 may include one or more receivers residing in, on or proximate the substrate. In some examples, the receiver system 102 may include at least one receiver element on the side of the substrate 101 where a light-emitting portion of the light source system 104 resides, which may sometimes be referred to herein as the "first side" of the substrate 101. According to some examples, the receiver system 102 may include at least one receiver element offset laterally from the area of the substrate (the area through which the light source system transmits light) in a first direction and at least one receiver element offset laterally from the area of the substrate in a second and opposite direction. In some examples, the receiver system 102 may include at least one interdigital transducer.

In some examples, the receiver system 102 may be configured to detect surface acoustic waves propagating in the substrate corresponding to a photoacoustic response of the target object to light emitted by the light source system. According to some examples, the photoacoustic response of the target object may include a photoacoustic response of a blood vessel, of blood within the blood vessel, or a combination thereof, within the target object. The blood vessel may, in some instances, be an artery. According to some examples, the photoacoustic response of the target object may produce target object acoustic waves within the target object. The target object acoustic waves may include longitudinal ultrasonic acoustic waves. At least some of the target object acoustic waves may be converted to the surface acoustic waves propagating in the substrate.

In some examples, the receiver system 102 may include piezoelectric material, such as lithium niobate ($LiNO_3$), lithium tantalate, lead magnesium niobate-lead titanate (PMM-PT), lithium tantalate, quartz, a polyvinylidene difluoride (PVDF) polymer, a polyvinylidene fluoride-trifluoroethylene (PVDF-TrFE) copolymer, a piezoelectric composite, etc. In some implementations, a single piezoelectric layer may serve as a surface acoustic wave receiver. In some implementations, other piezoelectric materials may be used in the piezoelectric layer, such as aluminum nitride (AlN) or lead zirconate titanate (PZT). In some examples, a type of piezoelectric crystal, a piezo-crystal cut, or both, may be selected to enhance the sensitivity of the receiver system 102 to one or more particular types of surface acoustic waves.

The control system 106 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 106 also may include (and/or be configured for communication with) one or more memory devices, such as one or more random access memory (RAM) devices, read-only memory (ROM) devices, etc. Accordingly, the apparatus 100 may have a memory system that includes one or more memory devices, though the memory system is not shown in FIG. 1. The control system 106 may be configured for receiving and processing data from the receiver system 102, e.g., as described below. If the apparatus 100 includes an ultrasonic transmitter, the control system 106 may be configured for controlling the ultrasonic transmitter. In some implementations, functionality of the control system 106 may be partitioned between one or more controllers or processors, such as a dedicated sensor controller and an applications processor of a mobile device.

In some examples, the control system 106 may be configured to control the light source system 104. For example, the control system 106 may be configured to control one or more light-emitting portions of the light source system 104 to emit laser pulses. The laser pulses may, in some examples, be in a wavelength range of 500 nm to 1000 nm. The laser pulses may, in some examples, have pulse widths in the range of 3 nanoseconds to 1000 nanoseconds.

In some examples, the control system 106 may be configured to receive signals from the receiver system 102 corresponding to the target ultrasonic waves generated by the target object responsive to the light from the light source system 104 and the surface acoustic waves produced by these target ultrasonic waves. According to some examples, the control system 106 may be configured to receive surface acoustic wave signals from the receiver system corresponding to detected surface acoustic waves and to detect at least one structure within the target object based on the surface acoustic wave signals. In some examples, the at least one structure may be a blood vessel structure, such as an arterial structure. In some instances, the surface acoustic wave signals may correspond with a photoacoustic response of a blood vessel, blood within the blood vessel, or a combination thereof, within the target object. In some examples, the control system 106 may be configured to estimate one or more cardiac-related features based, at least in part, on the surface acoustic wave signals. In some such examples, the control system 106 may be configured to estimate one or more cardiac-related features based, at least in part, on at least one structure detected within the target object according to the surface acoustic wave signals. In some such examples, the control system 106 may be configured to estimate one or more cardiac-related features based, at least in part, on changes in arterial distension caused by phases of the cardiac cycle and detected with the surface acoustic wave signals. According to some examples, the cardiac features may be, or may include, blood pressure.

Some implementations of the apparatus 100 may include the interface system 108. In some examples, the interface system 108 may include a wireless interface system. In some implementations, the interface system 108 may include a user interface system, one or more network interfaces, one or more interfaces between the control system 106 and a memory system and/or one or more interfaces between the control system 106 and one or more external device interfaces (e.g., ports or applications processors), or combinations thereof. According to some examples in which the interface system 108 is present and includes a user interface system, the user interface system may include a microphone system, a loudspeaker system, a haptic feedback system, a voice command system, one or more displays, or combinations thereof. According to some examples, the interface system 108 may include a touch sensor system, a gesture sensor system, or a combination thereof. The touch sensor system (if present) may be, or may include, a resistive touch sensor system, a surface capacitive touch sensor system, a projected capacitive touch sensor system, a surface acoustic wave touch sensor system, an infrared touch sensor system, any other suitable type of touch sensor system, or combinations thereof.

In some examples, the interface system 108 may include, a force sensor system. The force sensor system (if present) may be, or may include, a piezo-resistive sensor, a capacitive sensor, a thin film sensor (for example, a polymer-based thin film sensor), another type of suitable force sensor, or combinations thereof. If the force sensor system includes a piezo-resistive sensor, the piezo-resistive sensor may include silicon, metal, polysilicon, glass, or combinations thereof. In some examples, the interface system 108 may include an optical sensor system, one or more cameras, or a combination thereof.

The apparatus 100 may be used in a variety of different contexts, many examples of which are disclosed herein. For example, in some implementations a mobile device may include the apparatus 100. In some such examples, the mobile device may be a smart phone. In some implementations, a wearable device may include the apparatus 100. The wearable device may, for example, be a bracelet, an armband, a wristband, a watch, a ring, a headband or a patch.

Figure 2:
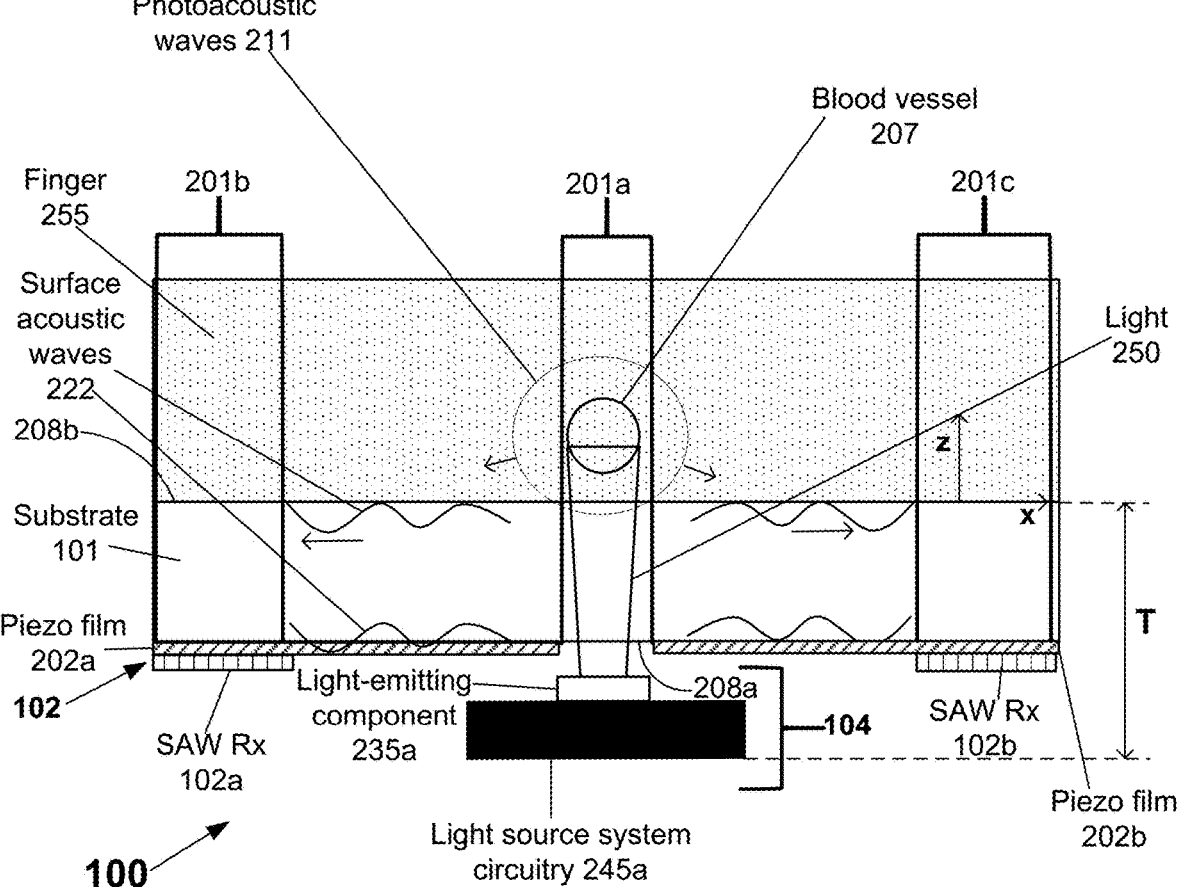
FIG. 2 shows example components of an apparatus according to some disclosed implementations.

FIG. 2 shows example components of an apparatus according to some disclosed implementations. As with other figures provided herein, the numbers, types and arrangements of elements shown in FIG. 2 are merely presented by way of example. In this example, the apparatus 100 is an instance of the apparatus 100 shown in FIG. 1. According to this example, the apparatus 100 includes a substrate 101, a receiver system 102 and a light source system 104.

In this example, an outer surface 208b of the substrate 101 is configured to receive a target object, such as the finger 255, a wrist, etc. In FIG. 2, only a portion of the finger 255 is shown. In this example, the substrate 101 includes substrate areas 201a, 201b and 201c. According to this example, at least the substrate area 201a is transparent, allowing light 250 from the light source system 104 to be transmitted from a first side of the substrate, which is proximate the light source system 104, towards-and in this example, into-a target object in contact with a second and opposite side of the substrate 101. In FIG. 2, the surface 208a is an example of the first side of the substrate 101 and the outer surface 208b is an example of the second side of the substrate 101. Accordingly, at least the area 201a of the substrate 101 includes a transparent material such as glass, acrylic, polycarbonate, etc.

In some examples, the substrate 101 may have a thickness in the range from 0.1 mm to 2 mm. According to some examples, the substrate 101 may have an acoustic impedance that is configured to contrast with an acoustic impedance of human skin. For example, the acoustic impedance of the substrate 101 may be configured to be substantially greater than that of human skin. A typical range of acoustic impedances for human skin is 1.53-1.680 MRayls. In some examples, the substrate 101 may have an acoustic impedance that is in the range of 2.5-16.0 MRayls, such as polycarbonate, glass, quartz or another piezoelectric crystal, etc.

According to this example, the receiver system 102, is, or includes, a surface acoustic wave receiver system that is configured to detect the surface acoustic waves 222. In this example, the receiver system 102 includes the surface acoustic wave receiver elements 102a and 102b, and the piezoelectric film layers 202a and 202b. According to this example, the surface acoustic wave receiver element 102a resides on the piezoelectric film layer 202a in a substrate area 201b. In this example, the surface acoustic wave receiver element 102b resides on the piezoelectric layer 202b in a substrate area 201c. Accordingly, in this example the receiver system 102 includes at least one surface acoustic wave receiver element offset laterally from the substrate area 201a in a first direction and at least one surface acoustic wave receiver element offset laterally from the substrate area 201a in a second and opposite direction. In some examples, the surface acoustic wave receiver elements 102a and 102b may include interdigital transducers. Some examples of suitable interdigital transducers are described herein with reference to FIG. 4.

The piezoelectric layers 202a and 202b may, for example, include a polyvinylidene difluoride (PVDF) polymer, a polyvinylidene fluoride-trifluoroethylene (PVDF-TrFE) copolymer, aluminum nitride (AlN), lead zirconate titanate (PZT), piezoelectric composite material, such as a 1-3 composite, a 2-2 composite, a 3-3 composite, etc., or combinations thereof. In some examples, the piezoelectric layers 202a and 202b may include one or more piezoelectric crystals, such as lithium niobate ($LiNO_3$), lithium tantalate, lead magnesium niobate-lead titanate (PMM-PT), lithium tantalate, quartz, etc.

According to some examples, the receiver system 102 may be configured to selectively detect surface acoustic waves propagating in the substrate corresponding to a photoacoustic response of the target object to light emitted by the light source system. In some such examples, a type of piezoelectric crystal, a piezo-crystal cut, or both, may be selected to enhance the sensitivity of the receiver system 102 to one or more particular types of surface acoustic waves. For example, 36 degree YX cut lithium tantalate is suitable for generating, or receiving, shear horizontal waves. A 128 degree YX cut of lithium niobate is suitable for generating, or receiving, Rayleigh waves. Accordingly, the receiver system 102 may be configured to be relatively more sensitive to one or more particular types of surface acoustic waves than to other types of surface acoustic waves.

Alternatively, or additionally, in some examples, the receiver system 102 may be configured to selectively detect a particular type of surface acoustic waves propagating in the substrate. In some examples, the selective detection may be made according to a selected range gate delay (RGD), which may be applied by the control system 106. The RGD may correspond to a time interval for detecting a particular type of surface acoustic waves propagating in the substrate corresponding to a photoacoustic response of the target object to light emitted by the light source system. Longitudinal acoustic waves, shear acoustic waves and Rayleigh acoustic waves generally have different velocities within the same medium. Accordingly, a receiver system 102 that is configured with a particular RGD may selectively detect, for example, shear horizontal waves corresponding to a photoacoustic response of a target object responsive to light from the light source system 104 and corresponding to a travel time based on the velocity of shear horizontal waves in the medium in which the shear horizontal waves are traveling. A receiver system 102 that is configured with another RGD may selectively detect Rayleigh waves corresponding to a photoacoustic response of a target object. This RGD may correspond to an expected travel time of the Rayleigh waves, based on the velocity of Rayleigh waves in the medium in which the Rayleigh waves are traveling. Alternatively, or additionally, in some examples the selective detection may be made according to characteristic features of shear horizontal waves, characteristic features of Rayleigh waves, etc., such as wave propagation type, wave shape, etc. For example, a control system may be configured to detect Rayleigh waves based, at least in part, on the retrograde, elliptical motion that is characteristic of near-surface Rayleigh waves.

According to this example, the light source system 104 includes at least a first light-emitting component (the light-emitting component 235a in this example) and light source system circuitry 245a. The light-emitting component 235a may, for example, include one or more light-emitting diodes, one or more laser diodes, one or more VCSELs, one or more edge-emitting lasers, one or more neodymium-doped yttrium aluminum garnet (Nd:YAG) lasers, or combinations thereof.

In this example, the light source system 104 is configured to emit light through the substrate area 201a. According to this example, the light source system 104 is configured to transmit light 250 through the substrate area 201a towards the finger 255, which is in contact with the substrate area 201a. In this example, a blood vessel 207, blood within the blood vessel 207, or both, produce the photoacoustic waves 211 responsive to the light 250. According to some examples, the blood vessel 207 may be an artery. In this example, the photoacoustic waves 211 are converted to the surface acoustic waves 222 in the substrate 101.

According to some examples, a control system 106 (not shown in FIG. 2) may be configured to estimate one or more cardiac-related features based, at least in part, on surface acoustic wave signals received from the receiver system 102 corresponding to a photoacoustic response of the blood vessel 207, of blood within the blood vessel 207, or combinations thereof. In some such examples, the control system 106 may be configured to detect changes in the diameter of the blood vessel 207 based on the surface acoustic wave signals. According to some examples, the blood vessel 207 may be an artery. In some such examples, the control system 106 may be configured to detect—based at least in part on surface acoustic wave signals—changes in arterial distension caused by phases of the cardiac cycle. In some examples, the control system may be able to estimate a pulse wave velocity (PWV) of a propagating pulse within the artery based, at least in part, on the surface acoustic wave signals. Some examples are described below with reference to FIGS. 8-10C.

In the example shown in FIG. 2, the apparatus 101 has a thickness (along the z axis) of T from the top of the substrate 101 to the base of the light source system circuitry 245a. In some examples, T may be in the range of 2 mm to 5 mm. According to some examples, the substrate 101 may have a thickness in the range of 0.1 mm to 1.5 mm. In some examples, the light source system 104 may have a thickness in the range of 0.5 mm to 1.5 mm. According to some examples, a distance between the light source system 104 and the surface 208a may be less than 1 mm.

Figure 3:
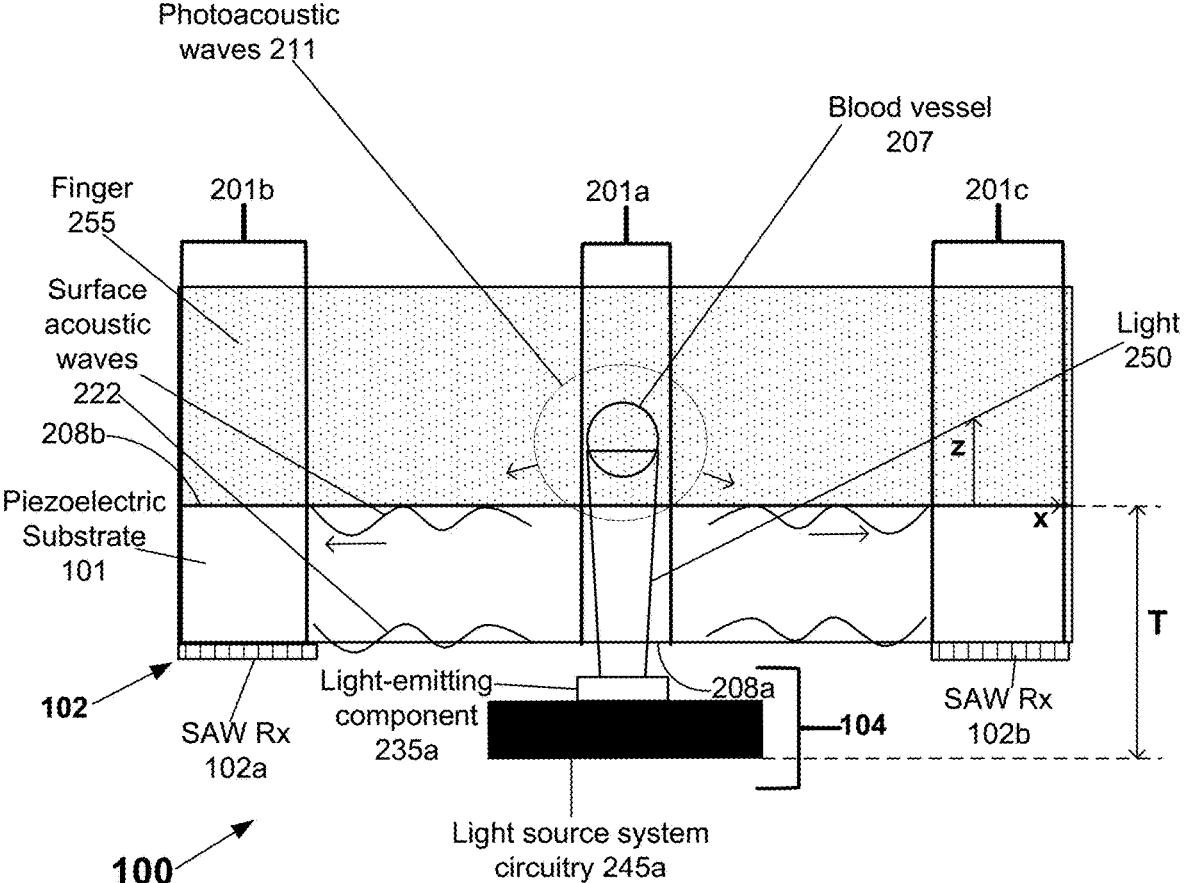
FIG. 3 shows example components of an apparatus according to some alternative implementations.

FIG. 3 shows example components of an apparatus according to some alternative implementations. As with other figures provided herein, the numbers, types and arrangements of elements shown in FIG. 3 are merely presented by way of example. In this example, the apparatus 100 is an instance of the apparatus 100 shown in FIG. 1. According to this example, the apparatus 100 includes a substrate 101, a receiver system 102 and a light source system 104.

The apparatus 101 shown in FIG. 3 is, in many ways, very similar to that shown in FIG. 2. Accordingly, all of the details will not be repeated here. Instead, the description of FIG. 3 will focus mainly on the differences between FIGS. 2 and 3.

According to this example, the receiver system 102, is, or includes, a surface acoustic wave receiver system that is configured to detect the surface acoustic waves 222. In this example, the receiver system 102 includes the surface acoustic wave receiver elements 102a and 102b. However, unlike the example shown in FIG. 2, in this example the receiver system 102 does not include the piezoelectric film layers 202a and 202b. According to this example, the substrate 101 itself is partially or completely formed of piezoelectric material. In such examples, the substrate 101 may be considered to be a part of the receiver system 102.

In some examples, the substrate 101 may include one or more piezoelectric crystals, such as lithium niobate (LiNO$_3$), lithium tantalate, lead magnesium niobate-lead titanate (PMM-PT), lithium tantalate, quartz, etc. In some such examples, the receiver system 102 may be configured to selectively detect the surface acoustic waves 222, for example as described above with reference to FIG. 2. In some examples, a type of piezoelectric crystal, a piezo-crystal cut, or both, may be selected to enhance the sensitivity of the receiver system 102 to one or more particular types of surface acoustic waves. In one such example, the substrate 101 may include a 128 degree YX cut of lithium niobate. As noted elsewhere herein, a 128 degree YX cut of lithium niobate is suitable for generating, or receiving, Rayleigh waves. In other implementations, the substrate 101 may include a different type of piezoelectric crystal, a different type of piezo-crystal cut, or combinations thereof. Accordingly, the receiver system 102 may be configured to be more sensitive to one or more particular types of surface acoustic waves based, at least in part, on piezoelectric material of the substrate 101.

Figure 4:
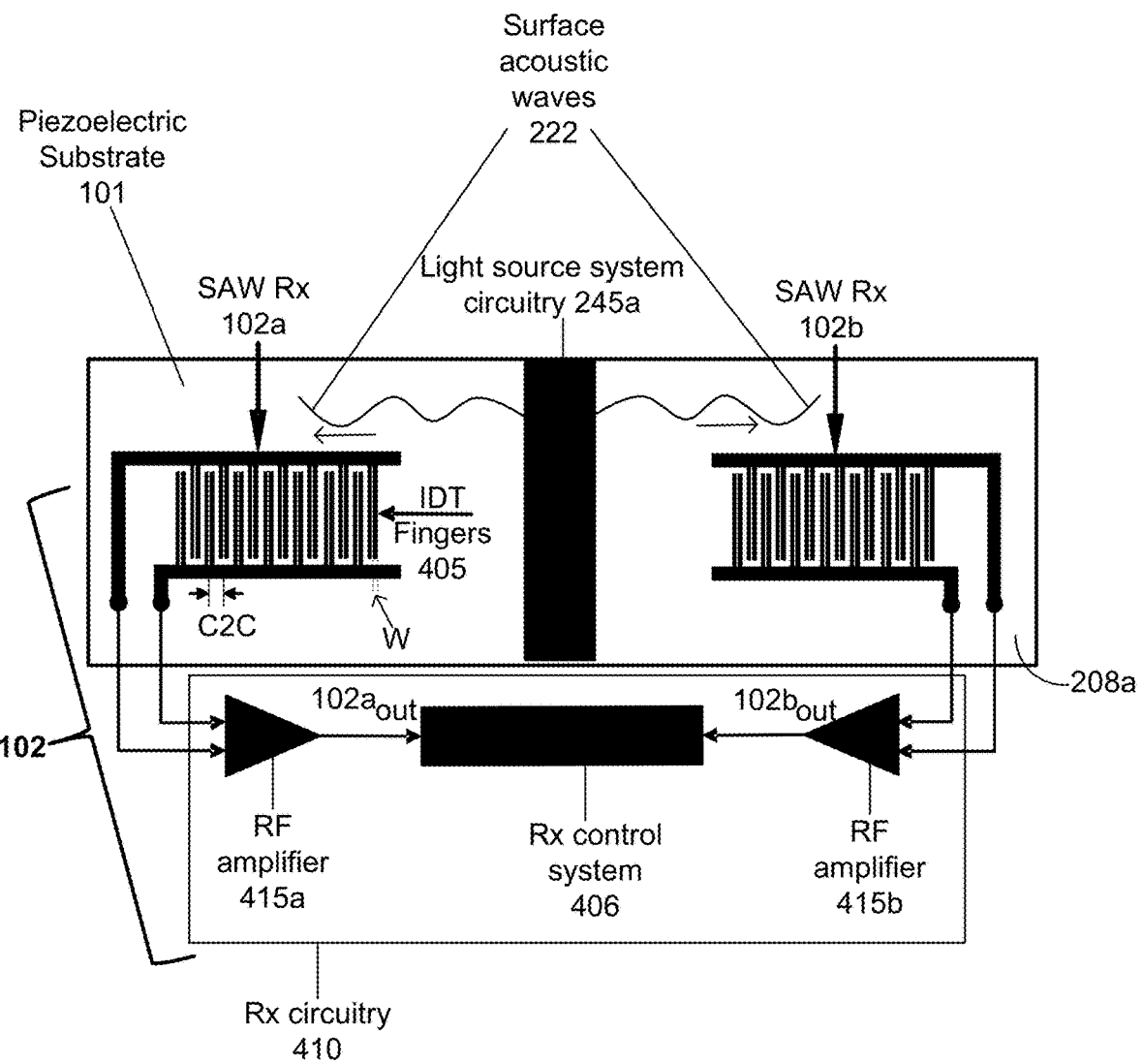
FIG. 4 shows a bottom view of example components of an apparatus according to some disclosed implementations.

FIG. 4 shows a bottom view of example components of an apparatus according to some disclosed implementations. As with other figures provided herein, the numbers, types and arrangements of elements shown in FIG. 4 are merely presented by way of example. In this example, the apparatus 100 is an instance of the apparatus 100 shown in FIG. 1. According to this example, the apparatus 100 includes a substrate 101, a receiver system 102 and a light source system 104.

Because FIG. 4 shows a bottom view, the view direction is towards the surface 208a of the substrate 101. As shown in FIGS. 2 and 3, the surface 208a is proximate the light source system 104, so the bottom of the light source system circuitry is shown in FIG. 4. In this example, the substrate 101 includes piezoelectric material, which may be substantially as described above with reference to FIG. 2 in some examples. In other examples, the substrate 101 may not include piezoelectric material. In some such examples, the piezoelectric film layers 202a and 202b of FIG. 2 would be visible in a bottom view like that of FIG. 4.

According to this example, the receiver system 102, is, or includes, a surface acoustic wave receiver system that is configured to detect the surface acoustic waves 222. In this example, the receiver system 102 includes the surface acoustic wave receiver elements 102a and 102b. According to this example, the surface acoustic wave receiver elements 102a and 102b include interdigital transducers (IDTs), the IDT fingers 405 of which are shown in FIG. 4. In some examples, the IDTs may be thin (such as less than 2 microns) metal electrodes deposited on the substrate 101, patterned and etched. In this example, the surface acoustic wave receiver elements 102a and 102b include IDT fingers 405 having a double-electrode or "split" electrode configuration. Other examples of the receiver system 102 may include other types of surface acoustic wave receiver elements, such as surface acoustic wave receiver elements having IDT fingers 405 in a single-electrode configuration.

The dimensions and layout of the IDT fingers 405 may depend, at least in part, on the type of IDT, the velocity of surface acoustic waves in the substrate 101 and the frequency or frequencies of interest. In some implementations of the substrate 101, the velocity of surface acoustic waves in the substrate 101 may be approximately 4000 m/s. In some examples, frequencies of interest may be in the range of 2 MHz to 10 Mhz. For a double-electrode configuration, it can be advantageous to have the width W of each of the double fingers to be $\lambda/8$ and the center-to-center (C2C) distance be $\lambda/4$, where $\lambda$ is a wavelength of received surface acoustic waves. For example, if the velocity of surface acoustic waves in the substrate 101 were 4000 m/s and a frequency of interest were 10 MHz., $\lambda$ would be 0.4 mm.

FIG. 4 also shows example components of receiver system circuitry 410. In this example, the receiver system circuitry 410 includes amplifiers 415a and 415b, which are radio frequency amplifiers in this example, and receiver system control system 406. According to this example, the amplifier 415a is configured to amplify the output signals "102a out" from the receiver element 102a and to provide corresponding amplified signals to the receiver system control system 406. Similarly, in this example the amplifier 415b is configured to amplify the output signals "102b out" from the receiver element 102b and to provide corresponding amplified signals to the receiver system control system 406. The control system 406 may, for example, be a component of the control system 106 that is described herein with reference to FIG. 1.

Figures 5A, 5B:
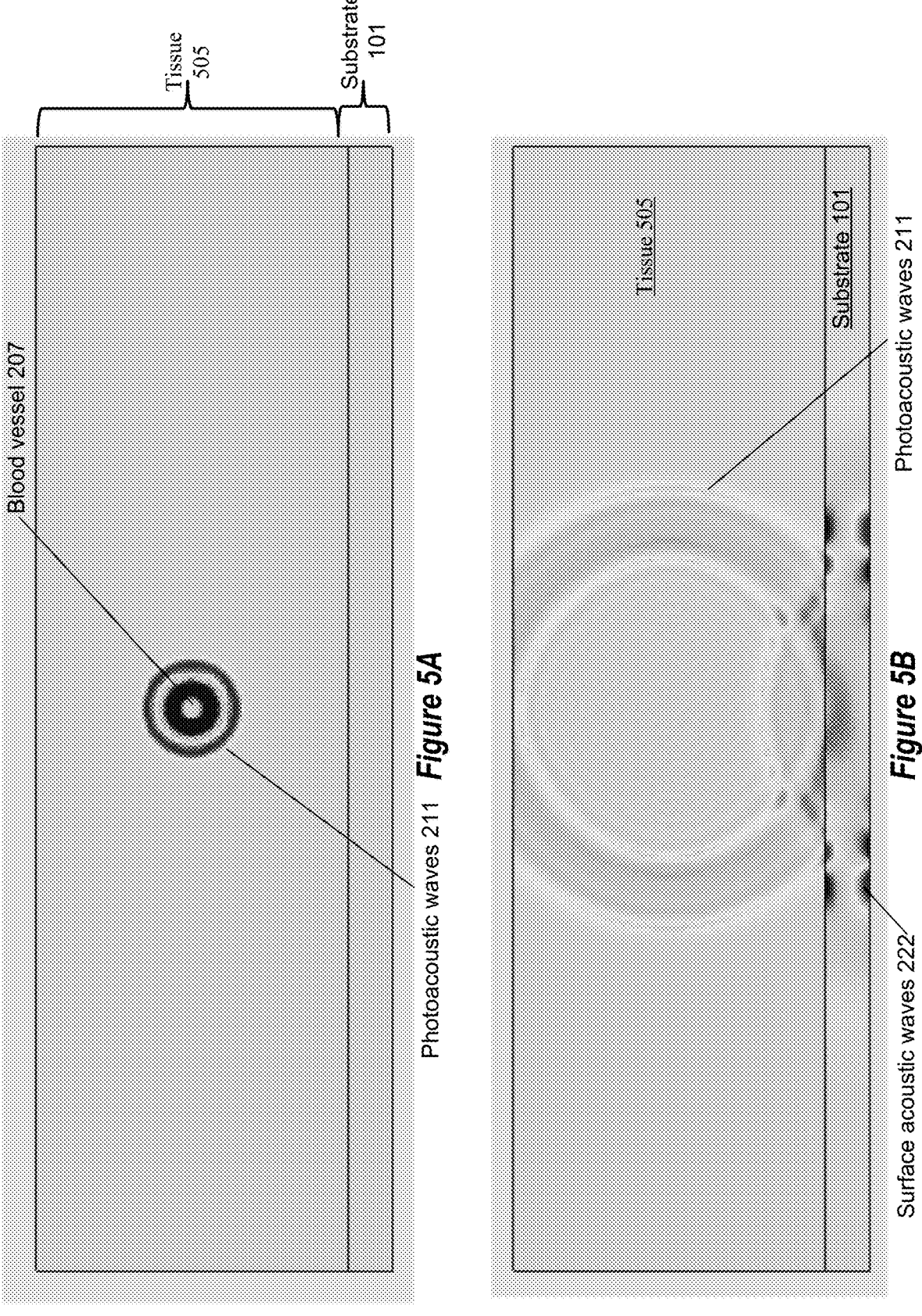
FIGS. 5A, 5B, 5C and 5D show examples of simulated photoacoustic waves and corresponding simulated surface acoustic waves.
Figures 5C, 5D:
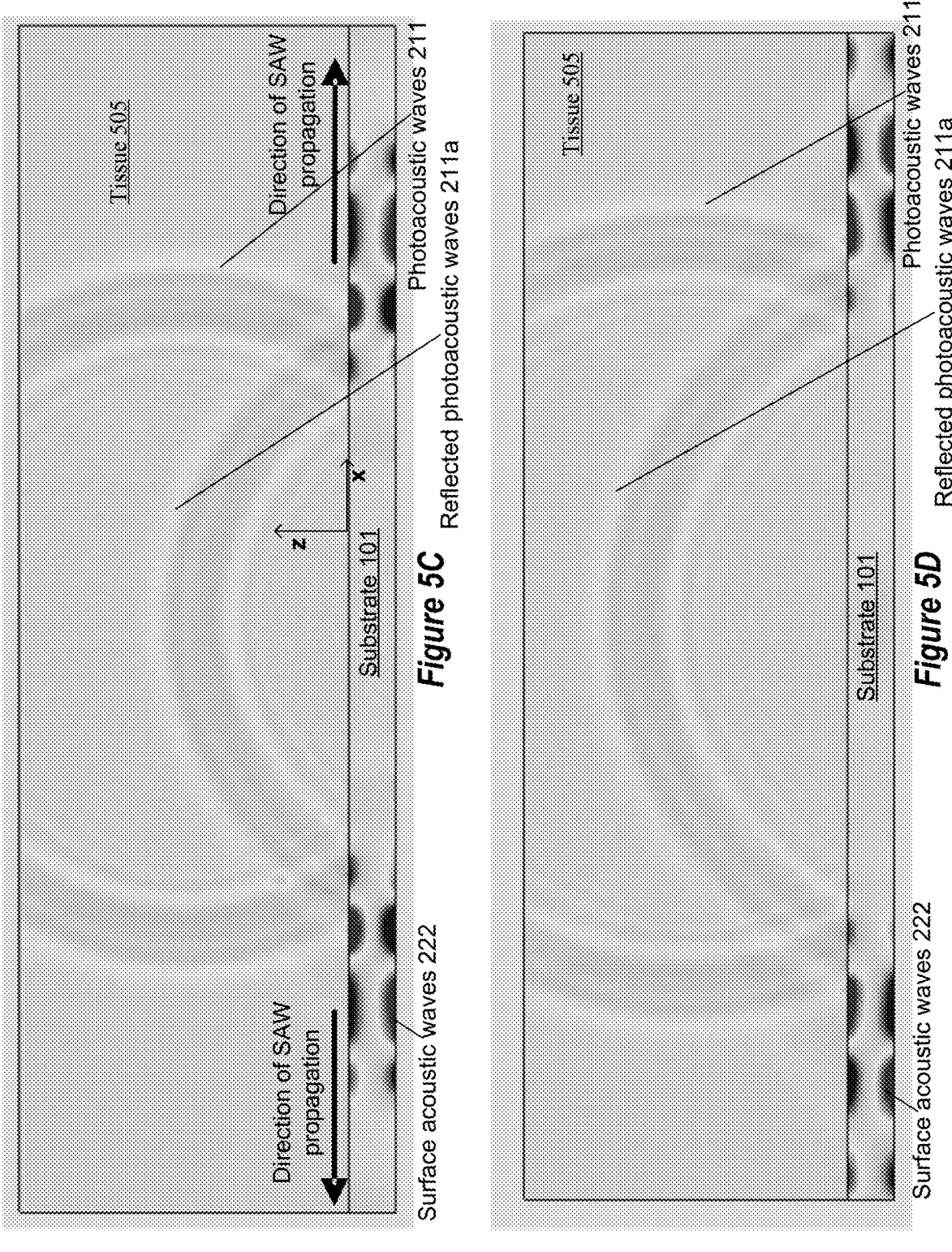

FIGS. 5A, 5B, 5C and 5D show examples of simulated photoacoustic waves and corresponding simulated surface acoustic waves. In these examples, FIG. 5A represents an instant in time of a simulation and FIGS. 5B-5D represent subsequent instants in time of the simulation. According to these examples, the tissue 505 is human tissue. In these examples, the substrate 101 is a piezoelectric substrate, which includes lithium niobate in this example, and has a thickness of 700 microns.

In the example shown in FIG. 5A, a blood vessel 207 within the tissue 505 has been illuminated with a laser pulse and is producing the photoacoustic waves 211. By the time corresponding to FIG. 5B, the photoacoustic waves 211 have propagated further within the tissue 505. Some of the photoacoustic waves 211 have reached the substrate 101 and have produced surface acoustic waves 222 within the substrate.

By the time corresponding to FIG. 5C, the photoacoustic waves 211 have reflected from the substrate 101, producing the reflected photoacoustic waves 211a. Moreover, the surface acoustic waves 222 have propagated within the substrate, substantially along the x axis in this view. The directions of surface acoustic wave (SAW) propagation are indicated by the labeled arrows. At the time corresponding to FIG. 5D, the photoacoustic waves 211, the reflected and the surface acoustic waves 222 have propagated further: some of the surface acoustic waves 222 have propagated to the outer edges of the substrate 101.

FIG. 6A is a flow diagram that shows examples of some disclosed operations. The blocks of FIG. 6A (and those of other flow diagrams provided herein) may, for example, be performed by the apparatus 100 of FIG. 1 or by a similar apparatus. As with other methods disclosed herein, the method outlined in FIG. 6A may include more or fewer blocks than indicated. Moreover, the blocks of methods disclosed herein are not necessarily performed in the order indicated. In some instances, one or more of the blocks shown in FIG. 6A may be performed concurrently.

In this example, block 605 involves controlling, by a control system, a light source system-which may be instances of the light source system 104 and the control system 106 of FIG. 1—to emit light through an area of a substrate, from a first side of the substrate towards a target object in contact with a second and opposite side of the substrate. In some examples, block 605 may involve controlling the light source system to emit one or more laser pulses. The target object may be a finger, a wrist, etc., depending on the particular example.

According to this example, block 610 involves receiving, by the control system and from a receiver system including one or more receivers residing in, on or proximate the substrate, surface acoustic wave signals corresponding to surface acoustic waves propagating in the substrate. The receiver system may be an instance of the receiver system 102 of FIG. 1, 2 or 3. Accordingly, in some examples, block 610 may involve receiving surface acoustic wave signals from the surface acoustic wave receiver elements 102a and 102b of FIG. 2, FIG. 3 or FIG. 4. In this example, the surface acoustic waves correspond to a photoacoustic response of the target object to light emitted by the light source system. The surface acoustic waves 222 of FIGS. 2, 3 and 5A-5D are examples of such surface acoustic waves.

According to this example, block 615 involves detecting, by the control system, at least one structure within the target object based on the surface acoustic wave signals. In some examples, the at least one structure may be, or may include, a blood vessel structure, such as an arterial structure. In some examples, method 600 may involve estimating one or more cardiac-related features based, at least in part, on the at least one structure.

FIG. 6B is a flow diagram that shows examples of some additional disclosed operations. The blocks of FIG. 6B (and those of other flow diagrams provided herein) may, for example, be performed by the apparatus 100 of FIG. 1 or by a similar apparatus. As with other methods disclosed herein, the method outlined in FIG. 6B may include more or fewer blocks than indicated. Moreover, the blocks of methods disclosed herein are not necessarily performed in the order indicated. In some instances, one or more of the blocks shown in FIG. 6B may be performed concurrently.

In this example, block 655 involves controlling, by a control system, a light source system to emit light towards a target object on, or proximate, an outer surface of a platen. The light source system and the control system may be instances of the light source system 104 and the control system 106 of FIG. 1. The target object may be a finger, a wrist, etc., depending on the particular example. According to this example, block 660 involves receiving, by the control system, signals from a surface acoustic wave receiver system-which may be an instance of the receiver system 102 of FIG. 1—corresponding to ultrasonic waves generated by the target object responsive to the light emitted by the light source system. The photoacoustic waves 211 of FIGS. 2, 3 and 5A-5D are examples of such ultrasonic waves. In some examples, block 660 may involve receiving signals from the surface acoustic wave receiver elements 102a and 102b of FIG. 2, FIG. 3 or FIG. 4.

According to this example, block 665 involves identifying, by the control system, blood vessel signals from the surface acoustic wave receiver system corresponding to ultrasonic waves generated by blood within a blood vessel of the target object, by one or more blood vessel walls, or combinations thereof. According to some examples, block 665 may involve identifying, by the control system, arterial signals from the surface acoustic wave receiver system corresponding to ultrasonic waves generated by blood within an artery of the target object by one or more arterial walls, or combinations thereof. The blood vessel signals may, for example, be identified by implementing a range gate delay (RGD) that corresponds with the expected depth to a blood vessel. Alternatively, or additionally, the arterial signals may be identified according to one or more characteristics of the photoacoustic responses of the blood vessel walls, blood, or a combination thereof. According to some examples, arterial signals may be distinguished from venial signals based, at least in part, on an estimated concentration of oxygenated hemoglobin ($HbO_2$) in the blood within the blood vessel.

In this example, block 670 involves estimating, by the control system, one or more cardiac features based, at least in part, on the blood vessel signals. In some examples, block 670 may involve estimating a blood pressure based, at least in part, on the blood vessel signals. In some such examples, block 670 may involve estimating a blood pressure based, at least in part, on arterial signals. According to some examples, block 670, or another aspect of method 650, may involve extracting and evaluating heart rate waveform (HRW) features.

Figure 7:
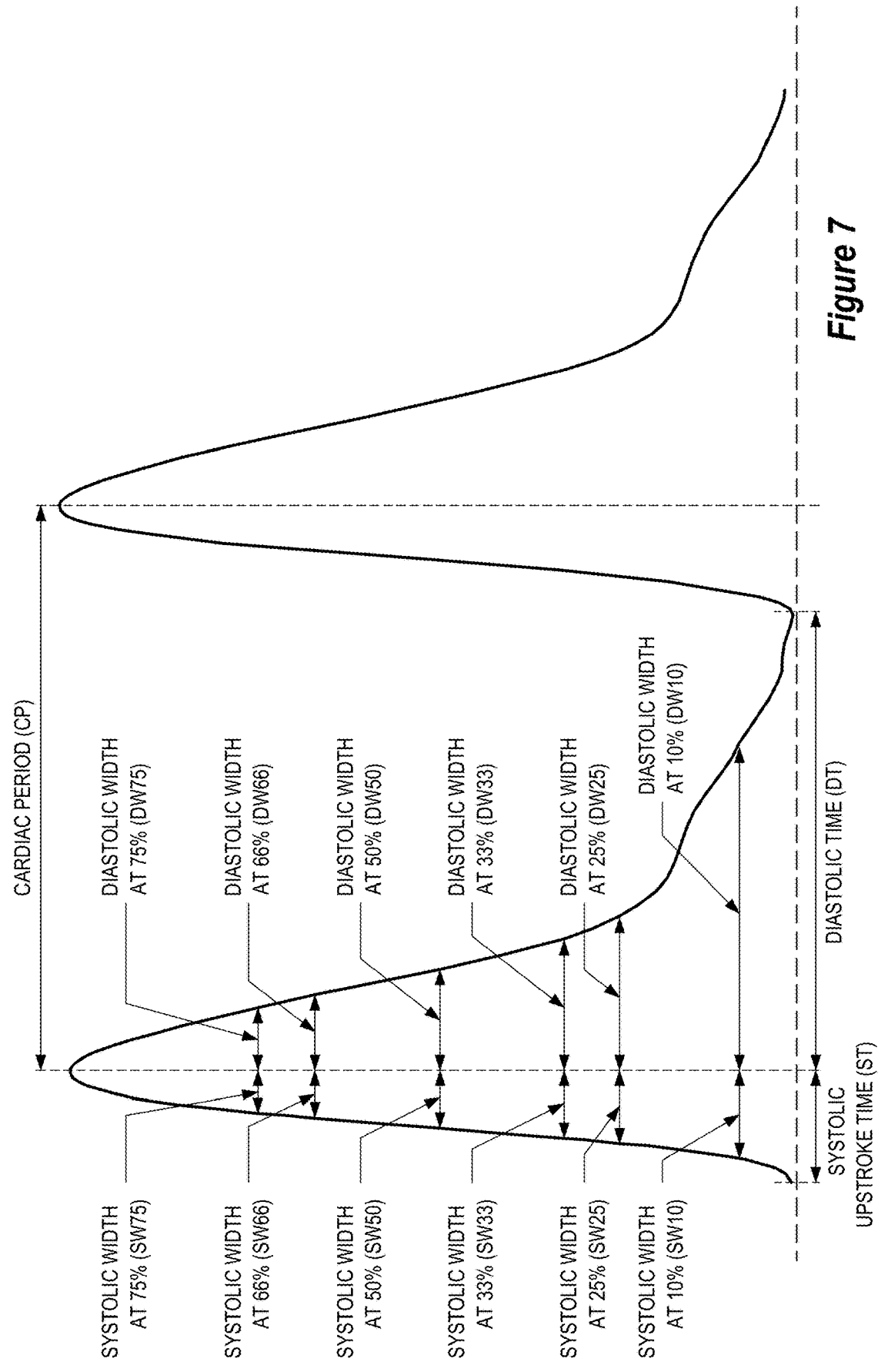
FIG. 7 shows examples of heart rate waveform (HRW) features that may be extracted according to some implementations of the method of FIG. 6A or the method of FIG. 6B.

FIG. 7 shows examples of heart rate waveform (HRW) features that may be extracted according to some implementations of the method of FIG. 6A or the method of FIG. 6B. The horizontal axis of FIG. 7 represents time and the vertical axis represents signal amplitude. The cardiac period is indicated by the time between adjacent peaks of the HRW. The systolic and diastolic time intervals are indicated below the horizontal axis. During the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

The HRW features that are illustrated in FIG. 7 pertain to the width of the systolic and/or diastolic portions of the HRW curve at various "heights," which are indicated by a percentage of the maximum amplitude. For example, the SW50 feature is the width of the systolic portion of the HRW curve at a "height" of 50% of the maximum amplitude. In some implementations, the HRW features used for blood pressure estimation may include some or all of the SW10, SW25, SW33, SW50, SW66, SW75, DW10, DW25, DW33, DW50, DW66 and DW75 HRW features. In other implementations, additional HRW features may be used for blood pressure estimation. Such additional HRW features may, in some instances, include the sum and ratio of the SW and DW at one or more "heights," e.g., (DW75+SW75), DW75/SW75, (DW66+SW66), DW66/SW66, (DW50+SW50), DW50/SW50, (DW33+SW33), DW33/SW33, (DW25+SW25), DW25/SW25 and/or (DW10+SW10), DW10/SW10. Other implementations may use yet other HRW features for blood pressure estimation. Such additional HRW features may, in some instances, include sums, differences, ratios and/or other operations based on more than one "height," such as (DW75+SW75)/(DW50+SW50), (DW50+SW50/(DW10+SW10), etc.

Figure 8:
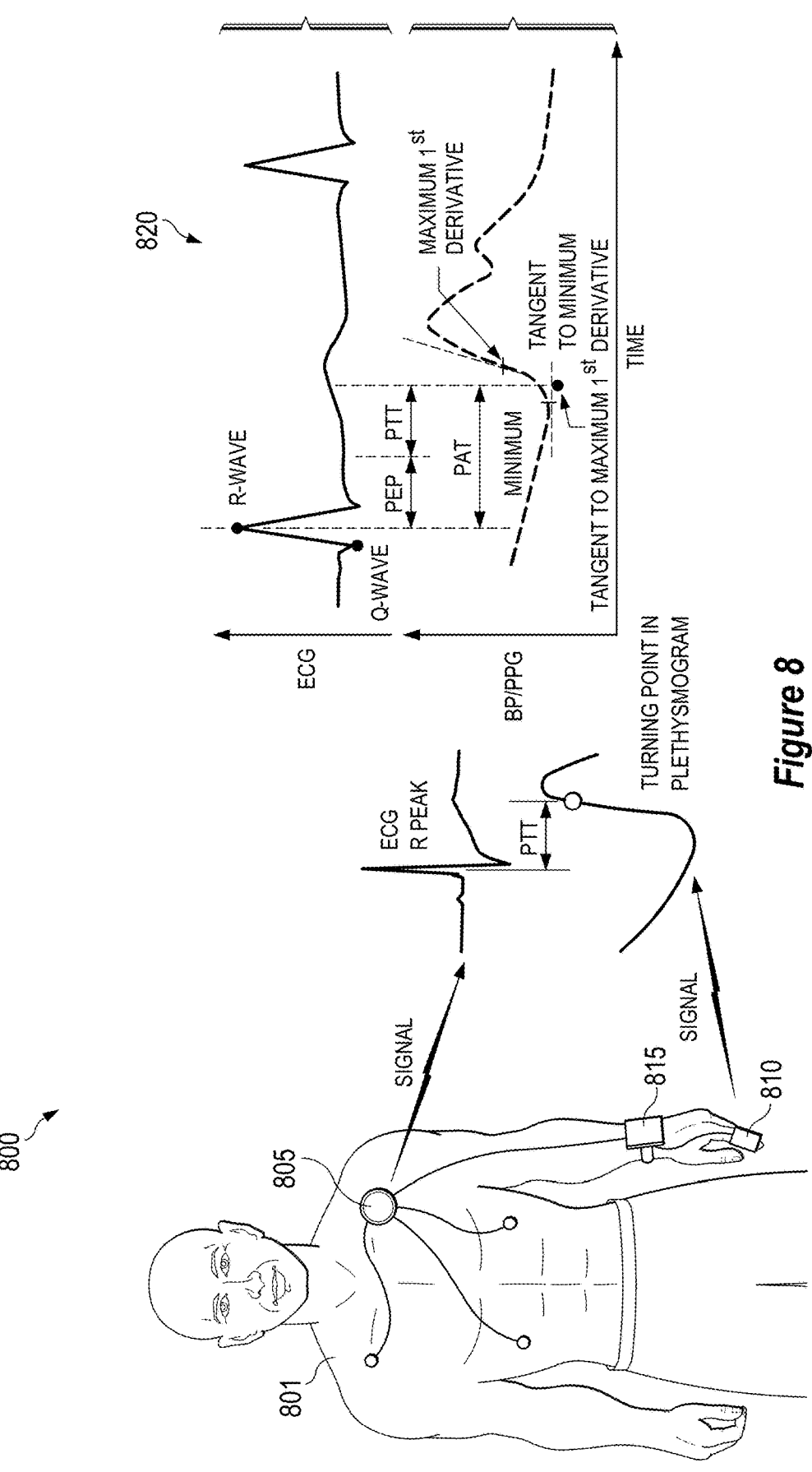
FIG. 8 shows examples of devices that may be used in a system for estimating blood pressure based, at least in part, on pulse transit time (PTT).

FIG. 8 shows examples of devices that may be used in a system for estimating blood pressure based, at least in part, on pulse transit time (PTT). As with other figures provided herein, the numbers, types and arrangements of elements are merely presented by way of example. According to this example, the system 800 includes at least two sensors. In this example, the system 800 includes at least an electrocardiogram sensor 805 and a device 810 that is configured to be mounted on a finger of the person 801. In this example, the device 810 is, or includes, an apparatus configured to perform at least some PAPG methods disclosed herein. For example, the device 810 may be, or may include, the apparatus 100 of FIG. 1 or a similar apparatus.

As noted in the graph 820, the pulse arrival time (PAT) includes two components, the pre-ejection period (PEP, the time needed to convert the electrical signal into a mechanical pumping force and isovolumetric contraction to open the aortic valves) and the PTT. The starting time for the PAT can be estimated based on the QRS complex—an electrical signal characteristic of the electrical stimulation of the heart ventricles. As shown by the graph 820, in this example the beginning of a PAT may be calculated according to an R-Wave peak measured by the electrocardiogram sensor 805 and the end of the PAT may be detected via analysis of signals provided by the device 810. In this example, the end of the PAT is assumed to correspond with an intersection between a tangent to a local minimum value detected by the device 810 and a tangent to a maximum slope/first derivative of the sensor signals after the time of the minimum value.

There are many known algorithms for blood pressure estimation based on the PTT and/or the PAT, some of which are summarized in Table 1 and described in the corresponding text on pages 5-10 of Sharma, M., et al., *Cuff-Less and Continuous Blood Pressure Monitoring: a Methodological*

*Review* ("Sharma"), in Multidisciplinary Digital Publishing Institute (MDPI) Technologies 2017, 5, 21, both of which are hereby incorporated by reference.

Some previously-disclosed methods have involved calculating blood pressure according to one or more of the equations shown in Table 1 of Sharma, or other known equations, based on a PTT and/or PAT measured by a sensor system that includes a PPG sensor. As noted above, some disclosed PAPG-based implementations are configured to distinguish artery HRWs from other HRWs. Such implementations may provide more accurate measurements of the PTT and/or PAT, relative to those measured by a PPG sensor. Therefore, disclosed PAPG-based implementations may provide more accurate blood pressure estimations, even when the blood pressure estimations are based on previously-known formulae.

Other implementations of the system 800 may not include the electrocardiogram sensor 805. In some such implementations, the device 815, which is configured to be mounted on a wrist of the person 801, may be, or may include, an apparatus configured to perform at least some PAPG methods disclosed herein. For example, the device 815 may be, or may include, the apparatus 200 of FIG. 2 or a similar apparatus. According to some such examples, the device 815 may include a light source system and two or more surface acoustic wave receivers. One example is described below with reference to FIG. 10A. In some examples, the device 815 may include an array of surface acoustic wave receivers.

In some implementations of the system 800 that do not include the electrocardiogram sensor 805, the device 810 may include a light source system and two or more surface acoustic wave receivers. One example is described below with reference to FIG. 10B.

Figure 9:
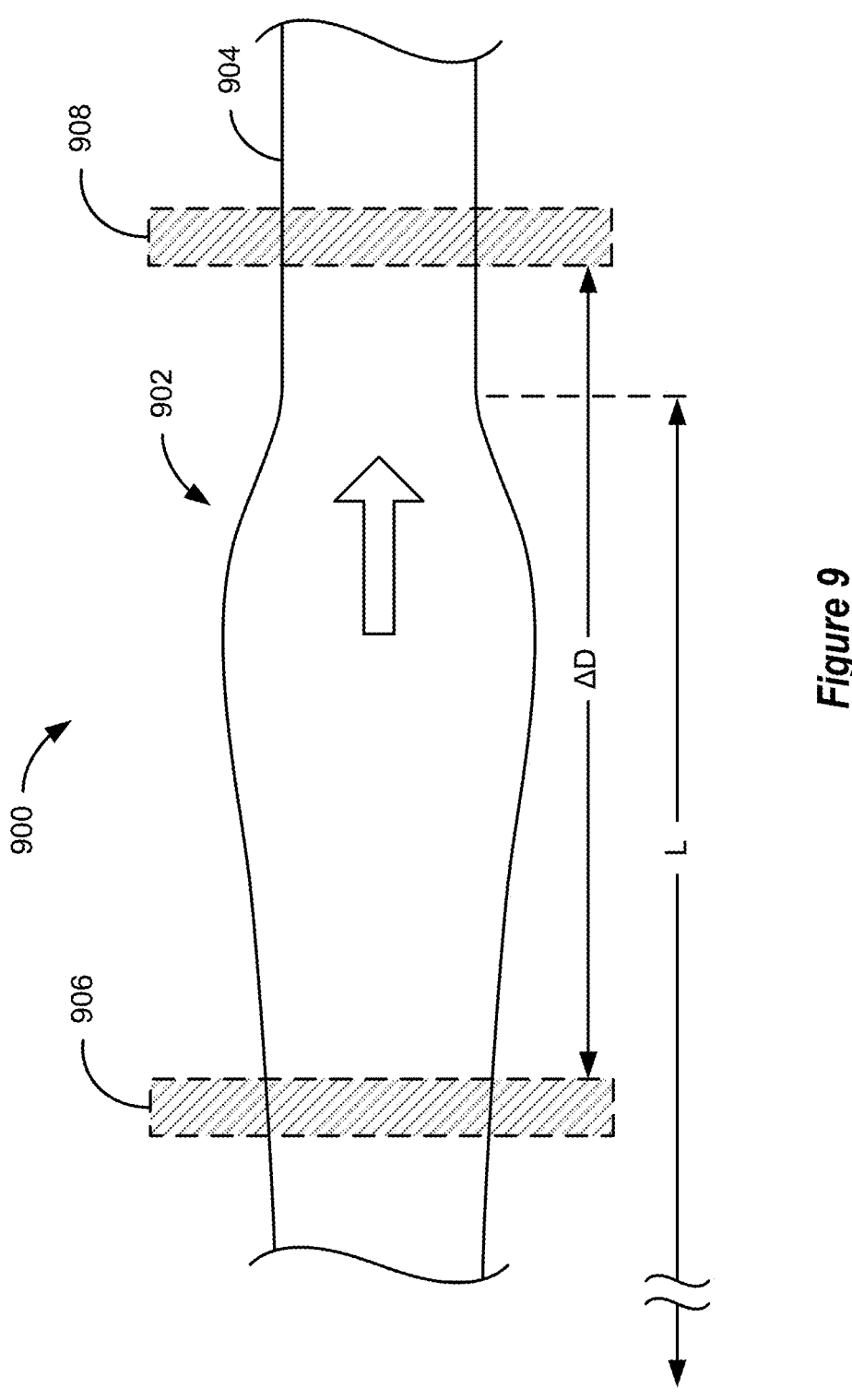
FIG. 9 shows a cross-sectional side view of a diagrammatic representation of a portion of an artery through which a pulse is propagating.

FIG. 9 shows a cross-sectional side view of a diagrammatic representation of a portion of an artery 900 through which a pulse 902 is propagating. The block arrow in FIG. 9 shows the direction of blood flow and pulse propagation. As diagrammatically shown, the propagating pulse 902 causes strain in the arterial walls 904, which is manifested in the form of an enlargement in the diameter (and consequently the cross-sectional area) of the arterial walls— referred to as "distension." The spatial length L of an actual propagating pulse along an artery (along the direction of blood flow) is typically comparable to the length of a limb, such as the distance from a subject's shoulder to the subject's wrist or finger, and is generally less than one meter (m). However, the length L of a propagating pulse can vary considerably from subject to subject, and for a given subject, can vary significantly over durations of time depending on various factors. The spatial length L of a pulse will generally decrease with increasing distance from the heart until the pulse reaches capillaries.

As described above, some particular implementations relate to devices, systems and methods for estimating blood pressure or other cardiovascular characteristics based on estimates of an arterial distension waveform. The terms "estimating," "measuring," "calculating," "inferring," "deducing," "evaluating," "determining" and "monitoring" may be used interchangeably herein where appropriate unless otherwise indicated. Similarly, derivations from the roots of these terms also are used interchangeably where appropriate; for example, the terms "estimate," "measurement," "calculation," "inference" and "determination" also are used interchangeably herein. In some implementations, the pulse wave velocity (PWV) of a propagating pulse may be estimated by measuring the pulse transit time (PTT) of the pulse as it propagates from a first physical location along an artery to another more distal second physical location along the artery. It will be appreciated that this PTT is different from the PTT that is described above. However, either version of the PTT may be used for the purpose of blood pressure estimation. Assuming that the physical distance $\Delta D$ between the first and the second physical locations is ascertainable, the PWV can be estimated as the quotient of the physical spatial distance $\Delta D$ traveled by the pulse divided by the time (PTT) the pulse takes in traversing the physical spatial distance $\Delta D$. Generally, a first sensor positioned at the first physical location is used to determine a starting time (also referred to herein as a "first temporal location") at which point the pulse arrives at or propagates through the first physical location. A second sensor at the second physical location is used to determine an ending time (also referred to herein as a "second temporal location") at which point the pulse arrives at or propagates through the second physical location and continues through the remainder of the arterial branch. In such examples, the PTT represents the temporal distance (or time difference) between the first and the second temporal locations (the starting and the ending times).

The fact that measurements of the arterial distension waveform are performed at two different physical locations implies that the estimated PWV inevitably represents an average over the entire path distance $\Delta D$ through which the pulse propagates between the first physical location and the second physical location. More specifically, the PWV generally depends on a number of factors including the density of the blood $\rho$, the stiffness of the arterial wall (or inversely the elasticity), the arterial diameter, the thickness of the arterial wall, and the blood pressure. Because both the arterial wall elasticity and baseline resting diameter (for example, the diameter at the end of the ventricular diastole period) vary significantly throughout the arterial system, PWV estimates obtained from PTT measurements are inherently average values (averaged over the entire path length $\Delta D$ between the two locations where the measurements are performed).

In traditional methods for obtaining PWV, the starting time of the pulse has been obtained at the heart using an electrocardiogram (ECG) sensor, which detects electrical signals from the heart. For example, the starting time can be estimated based on the QRS complex—an electrical signal characteristic of the electrical stimulation of the heart ventricles. In such approaches, the ending time of the pulse is typically obtained using a different sensor positioned at a second location (for example, a finger). As a person having ordinary skill in the art will appreciate, there are numerous arterial discontinuities, branches, and variations along the entire path length from the heart to the finger. The PWV can change by as much as or more than an order of magnitude along various stretches of the entire path length from the heart to the finger. As such, PWV estimates based on such long path lengths are unreliable.

In various implementations described herein, PTT estimates are obtained based on measurements (also referred to as "arterial distension data" or more generally as "sensor data") associated with an arterial distension signal obtained by each of a first arterial distension sensor 906 and a second arterial distension sensor 908 proximate first and second physical locations, respectively, along an artery of interest. In some particular implementations, the first arterial distension sensor 906 and the second arterial distension sensor 908 are advantageously positioned proximate first and second physical locations between which arterial properties of the artery of interest, such as wall elasticity and diameter, can be considered or assumed to be relatively constant. In this way, the PWV calculated based on the PTT estimate is more representative of the actual PWV along the particular segment of the artery. In turn, the blood pressure estimated based on the PWV is more representative of the true blood pressure. In some implementations, the magnitude of the distance ΔD of separation between the first arterial distension sensor 906 and the second arterial distension sensor 908 (and consequently the distance between the first and the second locations along the artery) can be in the range of about 1 centimeter (cm) to tens of centimeters—long enough to distinguish the arrival of the pulse at the first physical location from the arrival of the pulse at the second physical location, but close enough to provide sufficient assurance of arterial consistency. In some specific implementations, the distance ΔD between the first and the second arterial distension sensors 906 and 908 can be in the range of about 1 cm to about 30 cm, and in some implementations, less than or equal to about 20 cm, and in some implementations, less than or equal to about 10 cm, and in some specific implementations less than or equal to about 5 cm. In some other implementations, the distance ΔD between the first and the second arterial distension sensors 906 and 908 can be less than or equal to 1 cm, for example, about 0.1 cm, about 0.25 cm, about 0.5 cm or about 0.75 cm. By way of reference, a typical PWV can be about 15 meters per second (m/s). Using an ambulatory monitoring device in which the first and the second arterial distension sensors 906 and 908 are separated by a distance of about 5 cm, and assuming a PWV of about 15 m/s implies a PTT of approximately 3.3 milliseconds (ms).

The value of the magnitude of the distance ΔD between the first and the second arterial distension sensors 906 and 908, respectively, can be preprogrammed into a memory within a monitoring device that incorporates the sensors (for example, such as a memory of, or a memory configured for communication with, the control system 106 that is described above with reference to FIG. 1). As will be appreciated by a person of ordinary skill in the art, the spatial length L of a pulse can be greater than the distance ΔD from the first arterial distension sensor 906 to the second arterial distension sensor 908 in such implementations. As such, although the diagrammatic pulse 902 shown in FIG. 9 is shown as having a spatial length L comparable to the distance between the first arterial distension sensor 906 and the second arterial distension sensor 908, in actuality each pulse can typically have a spatial length L that is greater and even much greater than (for example, about an order of magnitude or more than) the distance ΔD between the first and the second arterial distension sensors 906 and 908.

Sensing Architecture and Topology

In some implementations of the ambulatory monitoring devices disclosed herein, both the first arterial distension sensor 906 and the second arterial distension sensor 908 are sensors of the same sensor type. In some such implementations, the first arterial distension sensor 906 and the second arterial distension sensor 908 are identical sensors. In such implementations, each of the first arterial distension sensor 906 and the second arterial distension sensor 908 utilizes the same sensor technology with the same sensitivity to the arterial distension signal caused by the propagating pulses, and has the same time delays and sampling characteristics. In some implementations, each of the first arterial distension sensor 906 and the second arterial distension sensor 908 is configured for photoacoustic plethysmography (PAPG)

sensing, e.g., as disclosed elsewhere herein. Some such implementations include a light source system and two or more surface acoustic wave receivers, which may be instances of the light source system 104 and the receiver system 102 of FIG. 1. In some implementations, each of the first arterial distension sensor 906 and the second arterial distension sensor 908 is configured for ultrasound sensing via the transmission of ultrasonic signals and the receipt of corresponding reflections. In some alternative implementations, each of the first arterial distension sensor 906 and the second arterial distension sensor 908 may be configured for impedance plethysmography (IPG) sensing, also referred to in biomedical contexts as bioimpedance sensing. In various implementations, whatever types of sensors are utilized, each of the first and the second arterial distension sensors 906 and 908 broadly functions to capture and provide arterial distension data indicative of an arterial distension signal resulting from the propagation of pulses through a portion of the artery proximate to which the respective sensor is positioned. For example, the arterial distension data can be provided from the sensor to a processor in the form of voltage signal generated or received by the sensor based on an ultrasonic signal or an impedance signal sensed by the respective sensor.

As described above, during the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

In the context of bioimpedance sensing (or impedance plethysmography), the blood in the arteries has a greater electrical conductivity than that of the surrounding or adjacent skin, muscle, fat, tendons, ligaments, bone, lymph or other tissues. The susceptance (and thus the permittivity) of blood also is different from the susceptances (and permittivities) of the other types of surrounding or nearby tissues. As a pulse propagates through a particular location, the corresponding increase in the volume of blood results in an increase in the electrical conductivity at the particular location (and more generally an increase in the admittance, or equivalently a decrease in the impedance). Conversely, during the diastolic phase of the cardiac cycle, the corresponding decrease in the volume of blood results in an increase in the electrical resistivity at the particular location (and more generally an increase in the impedance, or equivalently a decrease in the admittance).

A bioimpedance sensor generally functions by applying an electrical excitation signal at an excitation carrier frequency to a region of interest via two or more input electrodes, and detecting an output signal (or output signals) via two or more output electrodes. In some more specific implementations, the electrical excitation signal is an electrical current signal injected into the region of interest via the input electrodes. In some such implementations, the output signal is a voltage signal representative of an electrical voltage response of the tissues in the region of interest to the applied excitation signal. The detected voltage response signal is influenced by the different, and in some instances time-varying, electrical properties of the various tissues through which the injected excitation current signal is passed. In some implementations in which the bioimpedance sensor is operable to monitor blood pressure, heartrate or other cardiovascular characteristics, the detected voltage response signal is amplitude- and phase-modulated by the time-varying impedance (or inversely the admittance) of the underlying arteries, which fluctuates synchronously with the user's heartbeat as described above. To determine various biological characteristics, information in the detected voltage response signal is generally demodulated from the excitation carrier frequency component using various analog or digital signal processing circuits, which can include both passive and active components.

In some examples incorporating ultrasound sensors, measurements of arterial distension may involve directing ultrasonic waves into a limb towards an artery, for example, via one or more ultrasound transducers. Such ultrasound sensors also are configured to receive reflected waves that are based, at least in part, on the directed waves. The reflected waves may include scattered waves, specularly reflected waves, or both scattered waves and specularly reflected waves. The reflected waves provide information about the arterial walls, and thus the arterial distension.

In some implementations, regardless of the type of sensors utilized for the first arterial distension sensor 906 and the second arterial distension sensor 908, both the first arterial distension sensor 906 and the second arterial distension sensor 908 can be arranged, assembled or otherwise included within a single housing of a single ambulatory monitoring device. As described above, the housing and other components of the monitoring device can be configured such that when the monitoring device is affixed or otherwise physically coupled to a subject, both the first arterial distension sensor 906 and the second arterial distension sensor 908 are in contact with or in close proximity to the skin of the user at first and second locations, respectively, separated by a distance ΔD, and in some implementations, along a stretch of the artery between which various arterial properties can be assumed to be relatively constant. In various implementations, the housing of the ambulatory monitoring device is a wearable housing or is incorporated into or integrated with a wearable housing. In some specific implementations, the wearable housing includes (or is connected with) a physical coupling mechanism for removable non-invasive attachment to the user. The housing can be formed using any of a variety of suitable manufacturing processes, including injection molding and vacuum forming, among others.

In addition, the housing can be made from any of a variety of suitable materials, including, but not limited to, plastic, metal, glass, rubber and ceramic, or combinations of these or other materials. In particular implementations, the housing and coupling mechanism enable full ambulatory use. In other words, some implementations of the wearable monitoring devices described herein are noninvasive, not physically-inhibiting and generally do not restrict the free uninhibited motion of a subject's arms or legs, enabling continuous or periodic monitoring of cardiovascular characteristics such as blood pressure even as the subject is mobile or otherwise engaged in a physical activity. As such, the ambulatory monitoring device facilitates and enables long-term wearing and monitoring (for example, over days, weeks or a month or more without interruption) of one or more biological characteristics of interest to obtain a better picture of such characteristics over extended durations of time, and generally, a better picture of the user's health.

Figure 10A:
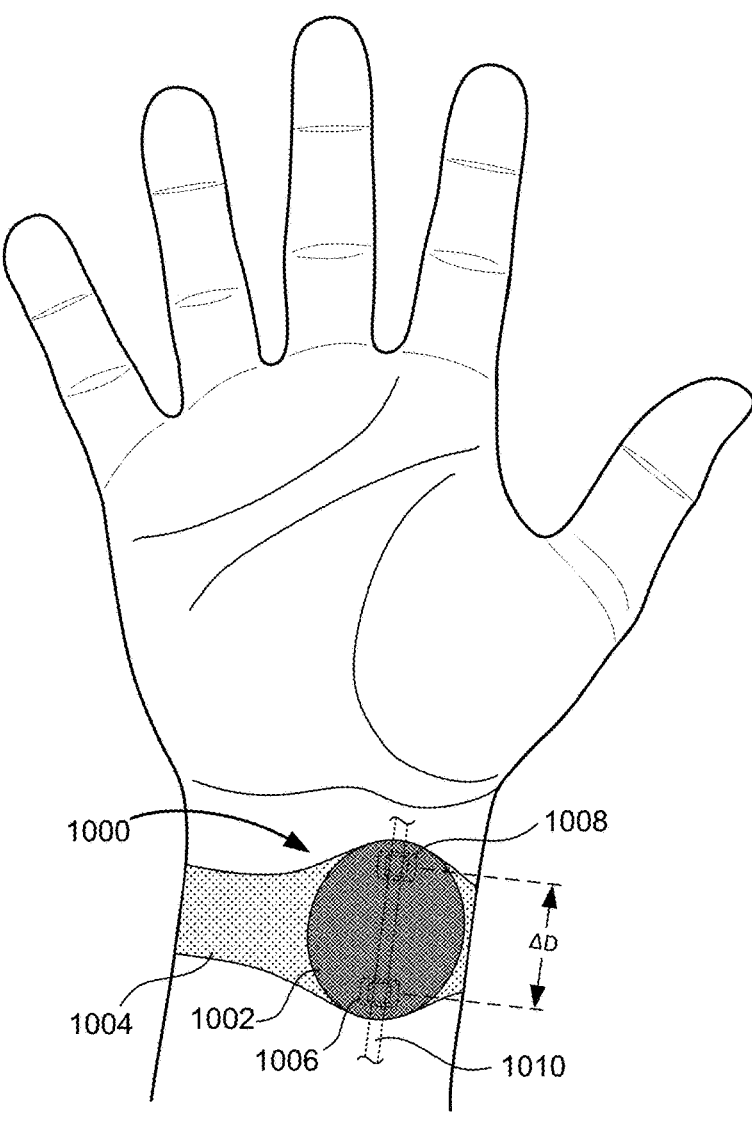
FIG. 10A shows an example ambulatory monitoring device designed to be worn around a wrist according to some implementations.

In some implementations, the ambulatory monitoring device can be positioned around a wrist of a user with a strap or band, similar to a watch or fitness/activity tracker. FIG. 10A shows an example ambulatory monitoring device 1000 designed to be worn around a wrist according to some implementations. In the illustrated example, the monitoring device 1000 includes a housing 1002 integrally formed with, coupled with or otherwise integrated with a wristband 1004. The first and the second arterial distension sensors 1006 and 1008 may, in some instances, each include instances of the surface acoustic wave receivers and the light source systems 104 that are described above with reference to FIGS. 1-4. In this example, the ambulatory monitoring device 1000 is coupled around the wrist such that the first and the second arterial distension sensors 1006 and 1008 within the housing 1002 are each positioned along a segment of the radial artery 1010 (note that the sensors are generally hidden from view from the external or outer surface of the housing facing the subject while the monitoring device is coupled with the subject, but exposed on an inner surface of the housing to enable the sensors to obtain measurements through the subject's skin from the underlying artery). Also as shown, the first and the second arterial distension sensors 1006 and 1008 are separated by a fixed distance ΔD. In some other implementations, the ambulatory monitoring device 1000 can similarly be designed or adapted for positioning around a forearm, an upper arm, an ankle, a lower leg, an upper leg, or a finger (all of which are hereinafter referred to as "limbs") using a strap or band.

Figure 10B:
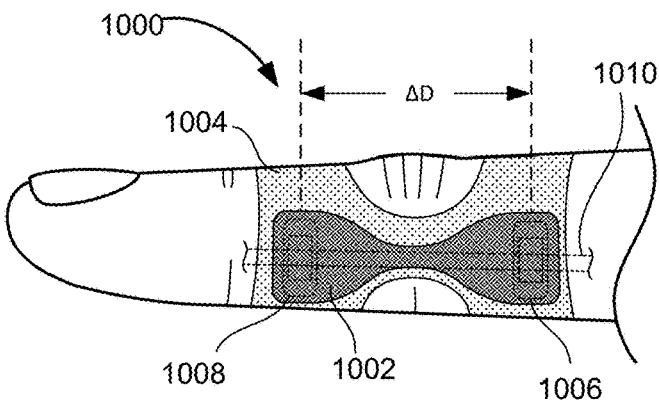
FIG. 10B shows an example ambulatory monitoring device designed to be worn on a finger according to some implementations.

FIG. 10B shows an example ambulatory monitoring device 1000 designed to be worn on a finger according to some implementations. The first and the second arterial distension sensors 1006 and 1008 may, in some instances, each include instances of the surface acoustic wave receivers and the light source systems 104 that are described above with reference to FIGS. 1-4.

In some other implementations, the ambulatory monitoring devices disclosed herein can be positioned on a region of interest of the user without the use of a strap or band. For example, the first and the second arterial distension sensors 1006 and 1008 and other components of the monitoring device can be enclosed in a housing that is secured to the skin of a region of interest of the user using an adhesive or other suitable attachment mechanism (an example of a "patch" monitoring device).

Figure 10C:
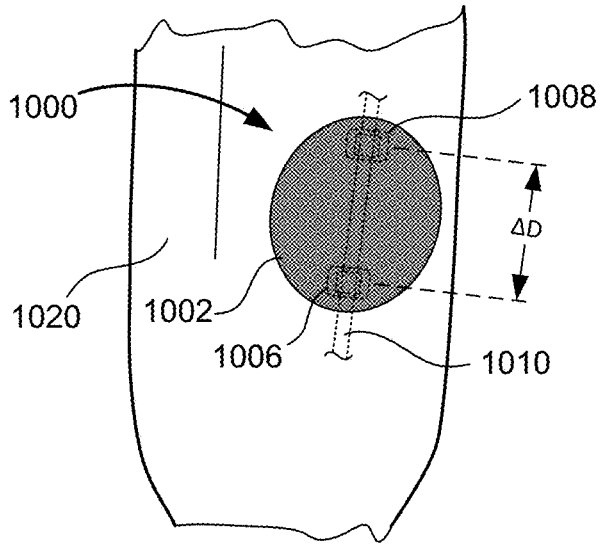
FIG. 10C shows an example ambulatory monitoring device designed to reside in or on an earbud according to some implementations.

FIG. 10C shows an example ambulatory monitoring device 1000 designed to reside in or on an earbud according to some implementations. According to this example, the ambulatory monitoring device 1000 is coupled to the housing of an earbud 1020. The first and second arterial distension sensors 1006 and 1008 may, in some instances, each include instances of the surface acoustic wave receivers and the light source systems 104 that are described above with reference to FIGS. 1-4.

Implementation examples are described in the following numbered clauses:

1. An apparatus, including: a substrate; a light source system configured to emit light through an area of the substrate, from a first side of the substrate towards a target object in contact with a second and opposite side of the substrate; a receiver system including one or more receivers residing in, on or proximate the substrate, the receiver system being configured to detect surface acoustic waves propagating in the substrate corresponding to a photoacoustic response of the target object to light emitted by the light source system; and a control system configured to: receive surface acoustic wave signals from the receiver system corresponding to detected surface acoustic waves; and detect at least one structure within the target object based on the surface acoustic wave signals.

2. The apparatus of clause 1, where the at least one structure is a blood vessel structure.

3. The apparatus of clause 1 or clause 2, where the control system is further configured to estimate one or more cardiac-related features based, at least in part, on the at least one structure.

4. The apparatus of any one of clauses 1-3, where the light source system is configured to emit laser pulses.

5. The apparatus of clause 4, where the laser pulses are in a wavelength range of 500 nm to 1000 nm.

6. The apparatus of clause 4 or clause 5, where the light source system is configured to emit the laser pulses at pulse widths in a range from 3 nanoseconds to 1000 nanoseconds.

7. The apparatus of any one of clauses 1-6, where the substrate is transparent.

8. The apparatus of any one of clauses 1-7, where the substrate includes piezoelectric material.

9. The apparatus of any one of clauses 1-8, where a combined thickness of the substrate and the light source system is in a range from 2 mm to 5 mm.

10. The apparatus of any one of clauses 1-9, where a thickness of the substrate is in a range from 0.5 mm to 1.0 mm.

11. The apparatus of any one of clauses 1-10, where a total area of the substrate is in a range from 0.5 cm2 to 2.0 cm2.

12. The apparatus of any one of clauses 1-11, where the receiver system includes piezoelectric material.

13. The apparatus of any one of clauses 1-12, where the receiver system includes at least one receiver element on the first side of the substrate.

14. The apparatus of any one of clauses 1-13, where the receiver system includes at least one receiver element offset laterally from the area of the substrate in a first direction and at least one receiver element offset laterally from the area of the substrate in a second and opposite direction.

15. The apparatus of any one of clauses 1-14, where the receiver system includes at least one interdigital transducer.

16. The apparatus of any one of clauses 1-15, where the control system is further configured to detect blood within a blood vessel based on the surface acoustic wave signals.

17. The apparatus of clause 16, where the blood vessel is an artery.

18. The apparatus of any one of clauses 1-17, where the photoacoustic response produces target object acoustic waves within the target object and where at least a portion of the target object acoustic waves is converted to the surface acoustic waves propagating in the substrate.

19. The apparatus of clause 18, where the target object acoustic waves include longitudinal ultrasonic acoustic waves.

20. An apparatus, including: a substrate; light source means for emitting light through an area of the substrate, from a first side of the substrate towards a target object in contact with a second and opposite side of the substrate; receiver means for detecting surface acoustic waves propagating in the substrate corresponding to a photoacoustic response of the target object to light emitted by the light source means; and control means for: receiving surface acoustic wave signals from the receiver means corresponding to detected surface acoustic waves; and detecting at least one structure within the target object based on the surface acoustic wave signals.

21. The apparatus of clause 20, where the at least one structure is a blood vessel structure.

22. The apparatus of clause 20 or clause 21, where the control means includes means for estimating one or more cardiac-related features based, at least in part, on the at least one structure.

23. The apparatus of any one of clauses 20-22, where the light source means is configured to emit laser pulses.

24. The apparatus of any one of clauses 20-23, where the substrate includes piezoelectric material.

25. The apparatus of any one of clauses 20-24, where a combined thickness of the substrate and the light source means is in a range from 2 mm to 5 mm.

26. The apparatus of any one of clauses 20-25, where the receiver means includes at least one receiver element on the first side of the substrate.

27. The apparatus of any one of clauses 20-26, where the receiver means includes at least one receiver element offset laterally from the area of the substrate in a first direction and at least one receiver element offset laterally from the area of the substrate in a second and opposite direction.

28. The apparatus of any one of clauses 20-27, where the receiver means includes at least one interdigital transducer.

29. A method, including: controlling, by a control system, a light source system to emit light through an area of a substrate, from a first side of the substrate towards a target object in contact with a second and opposite side of the substrate; receiving, by the control system and from a receiver system including one or more receivers residing in, on or proximate the substrate, surface acoustic wave signals corresponding to surface acoustic waves propagating in the substrate, the surface acoustic waves corresponding to a photoacoustic response of the target object to light emitted by the light source system; and detecting, by the control system, at least one structure within the target object based on the surface acoustic wave signals.

30. The method of clause 29, where the at least one structure is a blood vessel structure.

31. The method of clause 29 or clause 30, further including estimating one or more cardiac-related features based, at least in part, on the at least one structure.

32. The method of any one of clauses 29-31, where controlling the light source system involves controlling the light source system to emit laser pulses.

33. An apparatus, including: a substrate; a light source system configured to emit light through an area of the substrate, from a first side of the substrate towards a target object in contact with a second and opposite side of the substrate; and a receiver system including one or more receivers residing in, on or proximate the substrate, the receiver system being configured to selectively detect one or more specific types of surface acoustic waves propagating in the substrate corresponding to a photoacoustic response of the target object to light emitted by the light source system.

34. The apparatus of clause 33, where the receiver system includes at least one interdigital transducer.

35. The apparatus of clause 33 or clause 34, where the receiver system includes piezoelectric material.

36. The apparatus of clause 35, where the piezoelectric material includes a type of piezoelectric crystal that enhances a sensitivity of the receiver system to one or more particular types of surface acoustic waves.

37. The apparatus of clause 36, where the crystal has a piezo-crystal cut that enhances the sensitivity of the receiver system to the one or more particular types of surface acoustic waves.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single-or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

Various modifications to the implementations described in this disclosure may be readily apparent to those skilled in the art, and the generic principles defined herein may be applied to other implementations without departing from the scope of this disclosure. Thus, the following claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

What is claimed is:

1. An apparatus, comprising:
a substrate;
a light source system including one or more light-emitting diodes, one or more laser diodes, one or more vertical-cavity surface-emitting lasers (VCSELs), one or more edge-emitting lasers, one or more neodymium-doped yttrium aluminum garnet (Nd: YAG) lasers, or combinations thereof, the light source system being configured to emit light through an area of the substrate, from a first side of the substrate towards a target object in contact with a second and opposite side of the substrate;
a receiver system including one or more receivers residing in, on or proximate the substrate, the receiver system including piezoelectric material configured to detect acoustic wave signals, the acoustic wave signals including surface acoustic waves propagating in the substrate corresponding to a photoacoustic response of the target object to light emitted by the light source system; and
a control system including one or more general purpose single-or multi-chip processors, digital signal processors (DSPs), application specific integrated circuits (ASICs), field programmable gate arrays (FPGAs) or other programmable logic devices, discrete gates or transistor logic, discrete hardware components, or combinations thereof, the control system being configured to:
selectively detect surface acoustic wave signals from the receiver system corresponding to detected surface acoustic waves, wherein selectively detecting the surface acoustic wave signals involves distinguishing the surface acoustic wave signals from one or more other types of acoustic wave signals; and
detect at least one structure within the target object based only on the surface acoustic wave signals.

2. The apparatus of claim 1, wherein the at least one structure is a blood vessel structure.

3. The apparatus of claim 1, wherein the control system is further configured to estimate one or more cardiac-related features based, at least in part, on the at least one structure.

4. The apparatus of claim 1, wherein the light source system is configured to emit laser pulses.

5. The apparatus of claim 4, wherein the laser pulses are in a wavelength range of 500 nm to 1000 nm.

6. The apparatus of claim 4, wherein the light source system is configured to emit the laser pulses at pulse widths in a range from 3 nanoseconds to 1000 nanoseconds.

7. The apparatus of claim 1, wherein the substrate is transparent.

8. The apparatus of claim 1, wherein the substrate includes piezoelectric material.

9. The apparatus of claim 1, wherein a combined thickness of the substrate and the light source system is in a range from 2 mm to 5 mm.

10. The apparatus of claim 1, wherein a thickness of the substrate is in a range from 0.5 mm to 1.0 mm.

11. The apparatus of claim 1, wherein a total area of the substrate is in a range from 0.5 $cm^2$ to 2.0 $cm^2$.

12. The apparatus of claim 1, wherein the receiver system includes piezoelectric material.

13. The apparatus of claim 1, wherein the receiver system includes at least one receiver element on the first side of the substrate.

14. The apparatus of claim 1, wherein the receiver system includes at least one receiver element offset laterally from the area of the substrate in a first direction and at least one receiver element offset laterally from the area of the substrate in a second and opposite direction.

15. The apparatus of claim 1, wherein the receiver system includes at least one interdigital transducer.

16. The apparatus of claim 1, wherein the control system is further configured to detect blood within a blood vessel based on the surface acoustic wave signals.

17. The apparatus of claim 16, wherein the blood vessel is an artery.

18. The apparatus of claim 1, wherein the photoacoustic response produces target object acoustic waves within the target object and wherein at least a portion of the target object acoustic waves is converted to the surface acoustic waves propagating in the substrate.

19. The apparatus of claim 18, wherein the target object acoustic waves include longitudinal ultrasonic acoustic waves.

20. The apparatus of claim 1, wherein the one or more other types of acoustic wave signals correspond to longitudinal acoustic waves or shear acoustic waves detected by the receiver system.

21. The apparatus of claim 1, wherein the surface acoustic wave signals correspond to Rayleigh waves.

22. An apparatus, comprising:

a substrate;

light source means for emitting light through an area of the substrate, from a first side of the substrate towards a target object in contact with a second and opposite side of the substrate;

receiver means for detecting acoustic wave signals, the acoustic wave signals including surface acoustic waves propagating in the substrate corresponding to a photoacoustic response of the target object to light emitted by the light source means; and control means for:

selectively detecting surface acoustic wave signals from the receiver means corresponding to detected surface acoustic waves, wherein selectively detecting the surface acoustic wave signals involves distinguishing the surface acoustic wave signals from one or more other types of acoustic wave signals; and detecting at least one structure within the target object based only on the surface acoustic wave signals.

23. The apparatus of claim 22, wherein the at least one structure is a blood vessel structure.

24. The apparatus of claim 22, wherein the control means includes means for estimating one or more cardiac-related features based, at least in part, on the at least one structure.

25. The apparatus of claim 22, wherein the light source means is configured to emit laser pulses.

26. The apparatus of claim 22, wherein the substrate includes piezoelectric material.

27. The apparatus of claim 22, wherein a combined thickness of the substrate and the light source means is in a range from 2 mm to 5 mm.

28. The apparatus of claim 22, wherein the receiver means includes at least one receiver element on the first side of the substrate.

29. The apparatus of claim 22, wherein the receiver means includes at least one receiver element offset laterally from the area of the substrate in a first direction and at least one receiver element offset laterally from the area of the substrate in a second and opposite direction.

30. The apparatus of claim 22, wherein the receiver means includes at least one interdigital transducer.

31. A method, comprising:

controlling, by a control system, a light source system to emit light through an area of a substrate, from a first side of the substrate towards a target object in contact with a second and opposite side of the substrate;

receiving, by the control system and from a receiver system including one or more receivers residing in, on or proximate the substrate, acoustic wave signals, the acoustic wave signals including surface acoustic wave signals corresponding to surface acoustic waves propagating in the substrate, the surface acoustic waves corresponding to a photoacoustic response of the target object to light emitted by the light source system;

selectively detecting surface acoustic wave signals from the receiver system corresponding to detected surface acoustic waves, wherein selectively detecting the surface acoustic wave signals involves distinguishing the surface acoustic wave signals from one or more other types of acoustic wave signals; and detecting, by the control system, at least one structure within the target object based only on the surface acoustic wave signals.

32. The method of claim 31, wherein the at least one structure is a blood vessel structure.

33. The method of claim 31, further comprising estimating one or more cardiac-related features based, at least in part, on the at least one structure.

34. The method of claim 31, wherein controlling the light source system involves controlling the light source system to emit laser pulses.

35. An apparatus, comprising:

a substrate;

a light source system including one or more light-emitting diodes, one or more laser diodes, one or more vertical-cavity surface-emitting lasers (VCSELs), one or more edge-emitting lasers, one or more neodymium-doped yttrium aluminum garnet (Nd: YAG) lasers, or combinations thereof, the light source system being configured to emit light through an area of the substrate, from a first side of the substrate towards a target object in contact with a second and opposite side of the substrate;

a receiver system including one or more receivers residing in, on or proximate the substrate, the receiver system including piezoelectric material configured to selectively detect one or more specific types of surface acoustic waves propagating in the substrate corresponding to a photoacoustic response of the target object to light emitted by the light source system; and a control system including one or more general purpose single-or multi-chip processors, digital signal processors (DSPs), application specific integrated circuits (ASICs), field programmable gate arrays (FPGAs) or other programmable logic devices, discrete gates or transistor logic, discrete hardware components, or combinations thereof, the control system being configured to detect at least one structure within the target object based only on the one or more specific types of surface acoustic waves detected by the receiver system.

36. The apparatus of claim 35, wherein the receiver system includes at least one interdigital transducer.

37. The apparatus of claim 35, wherein the receiver system includes piezoelectric material.

38. The apparatus of claim 37, wherein the piezoelectric material includes a piezoelectric crystal that enhances a sensitivity of the receiver system to one or more particular types of surface acoustic waves.

39. The apparatus of claim 38, wherein the piezoelectric crystal has a piezo-crystal cut that enhances the sensitivity of the receiver system to the one or more particular types of surface acoustic waves.

40. The apparatus of claim 35, wherein selectively detecting the one or more specific types of surface acoustic waves involves distinguishing the surface acoustic waves from one or more other types of acoustic waves.

41. The apparatus of claim 40, wherein the one or more other types of acoustic waves include longitudinal acoustic waves or shear acoustic waves.

42. The apparatus of claim 35, wherein the one or more specific types of surface acoustic waves include Rayleigh waves.

* * * * *